(12) United States Patent
Wang et al.

(10) Patent No.: US 12,734,299 B2
(45) Date of Patent: Sep. 15, 2026

(54) FEEDBACK MECHANISMS

(71) Applicant: SHL MEDICAL AG, Zug (CH)

(72) Inventors: Hsuan Wang, Taoyuan City (TW); Ling-Hsiang Chao, Taipei (TW); Meng-Jhen Chiou, Taoyuan City (TW); Chia-Hsin Su, New Taipei City (TW); Tzu-Cheng Yeh, Taoyuan City (TW)

(73) Assignee: SHL Medical AG, Zug (CH)

(*) Notice: Subject to any disclaimer, the term of this patent is extended or adjusted under 35 U.S.C. 154(b) by 1039 days.

(21) Appl. No.: 17/774,935

(22) PCT Filed: Nov. 5, 2020

(86) PCT No.: PCT/EP2020/081037
§ 371 (c)(1),
(2) Date: May 6, 2022

(87) PCT Pub. No.: WO2021/110344
PCT Pub. Date: Jun. 10, 2021

(65) Prior Publication Data

US 2022/0387719 A1 Dec. 8, 2022

(30) Foreign Application Priority Data

| | | |
|---|---|---|
| Dec. 5, 2019 | (EP) | 19213746 |
| Dec. 19, 2019 | (EP) | 19217947 |
| Feb. 25, 2020 | (EP) | 20159266 |

(51) Int. Cl.
*A61M 5/315* (2006.01)
*A61M 5/20* (2006.01)

(52) U.S. Cl.
CPC ...... *A61M 5/31505* (2013.01); *A61M 5/2033* (2013.01); *A61M 5/3157* (2013.01);
(Continued)

(58) Field of Classification Search
CPC .. A61M 5/20; A61M 5/2033; A61M 5/31505; A61M 5/3157; A61M 5/31583;
(Continued)

(56) References Cited

U.S. PATENT DOCUMENTS

| | | | | |
|---|---|---|---|---|
| 8,734,402 B2* | 5/2014 | Sharp | A61M 5/002 604/223 |
| 9,457,154 B2 | 10/2016 | Moller et al. | |
| 10,220,154 B2 | 3/2019 | Marsh et al. | |
| 2014/0039407 A1 | 2/2014 | Schoonmaker | |

(Continued)

FOREIGN PATENT DOCUMENTS

| | | | |
|---|---|---|---|
| EP | 3141275 A1 | 3/2017 | |
| EP | 3184134 A1 * | 6/2017 | A61M 5/2033 |

(Continued)

OTHER PUBLICATIONS

International Search Report and Written Opinion for Int. App. No. PCT/EP2020/081037, mailed Mar. 9, 2021.

*Primary Examiner* — Michael J Tsai
*Assistant Examiner* — Forrest B Dipert
(74) *Attorney, Agent, or Firm* — McDonnell Boehnen Hulbert & Berghoff LLP

(57) ABSTRACT

A start of medicament delivery notification mechanism is presented where the notification mechanism is positioned within a housing of a medical device and includes a rear cap secured to a distal end of the housing, where the rear cap has a hollow tubular housing extending proximally from a distal end of the rear cap such that the tubular housing is cantilevered within and rotatably fixed relative to the housing and is parallel with a longitudinal axis of the housing. A rotator rotatably is positioned around the tubular housing such that rotator can rotate relative to the tubular housing from a first position to a second position, where the second position coincides with an initiation of a delivery of a dose of medicament. The rotator further has a contact surface that engages with and subsequently disengages from a corre-
(Continued)

sponding contact surface located on the rear cap or on an inside surface of the housing.

17 Claims, 15 Drawing Sheets

(52) U.S. Cl.
CPC ............... *A61M 2005/2013* (2013.01); *A61M 2005/31508* (2013.01); *A61M 2205/43* (2013.01); *A61M 2205/581* (2013.01); *A61M 2205/582* (2013.01)

(58) Field of Classification Search
CPC ............ A61M 5/31586; A61M 5/3204; A61M 5/326; A61M 5/3269; A61M 5/3271; A61M 5/3272; A61M 2005/31508; A61M 2005/3151; A61M 2005/2013; A61M 2005/3121; A61M 2005/3261; A61M 2005/3264; A61M 2005/3267
See application file for complete search history.

(56) References Cited

U.S. PATENT DOCUMENTS

| | | | |
|---|---|---|---|
| 2015/0032058 | A1 | 1/2015 | Karlsson |
| 2016/0106923 | A1 | 4/2016 | Brereton et al. |
| 2016/0121052 | A1 | 5/2016 | Burren et al. |
| 2018/0015227 | A1 | 1/2018 | Al-Omar |
| 2018/0021518 | A1 | 1/2018 | Avery et al. |
| 2018/0154083 | A1 | 6/2018 | Stewart |
| 2018/0339109 | A1 | 11/2018 | Halseth |

FOREIGN PATENT DOCUMENTS

| | | | | |
|---|---|---|---|---|
| EP | 3393551 | B1 | 6/2021 | |
| WO | 2010/126432 | A1 | 11/2010 | |
| WO | 2011/123024 | A1 | 10/2011 | |
| WO | 2011/139212 | A1 | 11/2011 | |
| WO | WO-2013032389 | A1 * | 3/2013 | .......... A61M 5/2033 |
| WO | 2014/139916 | A1 | 9/2014 | |
| WO | 2016/169756 | A1 | 10/2016 | |
| WO | 2016/193343 | A1 | 12/2016 | |
| WO | 2017/191159 | A1 | 11/2017 | |
| WO | WO-2017211531 | A1 * | 12/2017 | ............. G09B 23/00 |
| WO | WO2018/082887 | A1 | 5/2018 | |

* cited by examiner 5
5a
50
51
56

59
17
55
58

50
57a
57b
56
55

120
162
134
132
135
130
163
138
130
130
140
136
139

162
142
141
140
144
120
①
②
③
④
⑤
D1
D2

220
210
233

220

220
234
D'
240
210
233

FEEDBACK MECHANISMS

CROSS REFERENCE TO RELATED APPLICATIONS

The present application is a U.S. National Phase Application pursuant to 35 U.S.C. § 371 of International Application No. PCT/EP2020/081037 filed Nov. 5, 2020, which claims priority to EP patent application 19213746.1, EP patent application 20159266.4 and EP patent application 19217947.1. The entire disclosure contents of these applications are herewith incorporated by reference into the present application.

TECHNICAL FIELD

The present disclosure concerns medicament delivery devices, and particularly solutions related to feedback mechanisms for medicament delivery devices.

BACKGROUND

Medicament delivery devices such as those described in WO 2011/123024 have already been very commercially successful due to a combination of properties such as robustness, simplicity and usability. Nevertheless, the applicant has appreciated that there is still further scope for improvement of the feedback features in medicament delivery devices such as those described in WO 2011/123024.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

In one non-limiting embodiment of the present disclosure there is presented a start of medicament delivery notification mechanism that is located and positioned within a housing of a medical device, where the delivery notification mechanism includes a rear cap secured to a distal end of the housing and where the rear cap comprises a hollow tubular housing extending proximally from a distal end of the rear cap. The tubular housing preferably is cantilevered within and rotatably fixed relative to the housing and is positioned parallel to the longitudinal axis of the housing. A rotator is rotatably positioned around the tubular housing such that rotator can rotate relative to the tubular housing, moving from a first position to a second position during activation of the device, where attainment of the second position coincides with the initiation of the delivery of a dose of medicament from the device, for example through an injection needle. The rotator has a contact surface that engages with and subsequently disengages from a corresponding contact surface that is located 1) on the rear cap or 2) on an inside surface of the housing as the rotator moves from the first position to the second position. The disengagement of the contact surface from the corresponding contact surface is what causes an audible or tactile feedback that represents a notification to the user that medicament delivery has begun.

The rear cap of the feedback mechanism can also contain a flexible arm positioned on the tubular housing and can have an inner protrusion that is directed radially inward. This flexible arm can be configured to releasably engage with a plunger rod to hold the plunger rod axially fixed relative to the housing when the rotator is in the first position. Additionally, the flexible arm can generate feedback upon initiation of the medicament delivery when the rotator reaches the second position.

In another embodiment of the present disclosure there is presented a medical device having a start of dose delivery notification mechanism, where the medical device has a housing having a longitudinal axis, a distal end and a proximal end, where the distal end is open. A rear cap is secured to the distal end of the housing and has a distal end configured to fit into the open distal end of the housing. The rear cap further has a hollow tubular housing that extends proximally from the distal end of the rear cap such that the tubular housing is cantilevered within and rotatably fixed relative to the housing and is positioned parallel to the longitudinal axis. A flexible arm can be fixed to or integral with the tubular housing and can have an inner protrusion that is directed radially inward. A rotator can be rotatably positioned around the tubular housing such that rotator can rotate relative to the tubular housing from a first position to a second position. A plunger rod can be engaged with and held axially fixed relative to the housing by the flexible arm when the rotator is in the first position.

The rotator in the above embodiment can include an inward directed nib that engages the flexible arm when the rotator rotates from the first to the second position causing the flexible arm to move such that an audible or tactile feedback is emitted once the rotator has reached the second position. During rotation of the rotator preferably the flexible arm is moved transversely relative to the tubular housing. The flexible arm can also have an outer protrusion that is directed radially outward such that it can engage the nib on the inside surface of the rotator. The engagement of the nib with the outer protrusion can occur during rotation of the rotator from the first to second position such that the flexible arm is moved transversely in a first direction. The disengagement of the nib from the outer protrusion causes the flexible arm to move transversely in a second direction where it strikes a cut-out wall of the rotator. Preferably the flexible arm is positioned in a cut-out of a wall of the tubular housing and the flexible arm strikes the wall of the tubular housing to cause the audible or tactile feedback.

The flexible arm can have a distal end fixed to the tubular housing and a free proximal end positioned within the cut-out of the tubular housing, where the flexible arm is tapered such that the proximal end has a smaller width than the distal end. The inner and outer protrusions are also preferably positioned at the proximal end of the flexible arm.

The medical device described above can also have a needle cover that moves axially during activation relative to the housing to cause the rotator to move from the first to the second position.

In another embodiment of a start of delivery feedback mechanism contained within a medical device as similarly described above, the rotator can have a flexible lever where rotation of the rotator from the first to the second position causes the flexible lever to engage the inner surface of the housing such that an audible or tactile feedback is emitted once the rotator has reached the second position. In this embodiment the flexible lever is biased radially outward toward the inner surface of the housing, which can have a ramp or other perturbation that is configured to engage with the lever in fashion similar to how a follower and a cam surface interact with each other. The flexible lever is preferably configured and designed such that it rides up the ramp during rotation of the rotator. Upon disengagement of the lever and the ramp, the flexible lever will strike the inner surface of the housing causing the audible or tactile feedback that notifies the user that the delivery of the medicament from the medical device has commenced. The flexible lever can be also be configured to have an outwardly projecting knob, where the knob engages the inner surface of the housing during rotation of the rotator. Further, the lever can be positioned parallel to or transversely with the longitudinal axis of the housing and the rotator.

In yet another embodiment of the feedback mechanism of the present disclosure the hollow tubular housing of the rear cap can have one or more blocks located on the proximal end of the tubular housing. And, the rotator can be configured with a proximal end that has one or more ramped surfaces that are preferably circumferentially arranged around the terminal end surface of the rotator. The rotation of the rotator from the first to the second position causes at least one block to engage at least one of the ramped surfaces causing a slight axial movement of the rotator in a distal direction relative to rear cap. Disengagement of the block from the ramped surface causes an audible or tactile feedback. The audible or tactile feedback results from the proximal end of the rotator striking the block. The rear cap can also have one or more proximally projecting fingers that engage a distal end of the rotator such that the projecting finger flexes radially outward during rotation of the rotator as the rotator moves axially in the distal direction as the block and ramped surface engage and move relative to each other. The projecting fingers can contain a hook that engages and holds an inside surface of the distal end of the rotator during rotation from the first to the second position.

An additional embodiment of the present disclosure is directed to a start of delivery feedback mechanism where one or more flexible fingers project proximally from the distal end of the rear cap and the inside surface of the rotator has an inwardly directed protrusion that engages at least one of the flexible fingers as the rotator moves from the first position to the second position such that a proximal end of the finger will strike the rotator causing an audible or tactile feedback once the rotator has reached the second position.

Another aspect of the present disclosure concerns a rotator for a medicament delivery device, the rotator comprising: a tubular body extending from a proximal end to a distal end in an axial direction relative to an axis; one or more ridges extending from a surface of the tubular body, the one or more ridges defining a track on the surface of the tubular body, the track extending in the axial direction from a distal end of the track to a proximal end of the track, the track comprising one pathway at the distal end of the track and two pathways at the proximal end of the track, wherein the two pathways at the proximal end of the track are separated by at least one of the one or more ridges; and a protrusion extending from the surface of the track, the protrusion comprising a surface extending in the track, the surface of the protrusion comprising a first sloped portion and a second sloped portion closer to the distal end of the tubular body than the first sloped portion, wherein the first sloped portion and the second sloped portion are angled relative to the surface of the track, wherein the first sloped portion is angled towards the proximal end of the tubular body and the second sloped portion is angled towards the distal end of the tubular body. This can allow for a first click when the rotator is used within a medicament delivery device.

In one embodiment, the rotator comprises a tongue, and the protrusion is on the tongue, wherein the tongue extends in an opening in the surface in the track, and wherein the tongue is configured to flex relative to the surface of the track.

In one embodiment, the tongue extends in the axial direction from a proximal end to a distal end, and the proximal end of the tongue is attached to the tubular body and the distal end of the tongue is configured to flex relative to the surface of the track. In one embodiment, the tongue extends in the axial direction from a proximal end to a distal end, and the distal end of the tongue is attached to the tubular body and the proximal end of the tongue is configured to flex relative to the surface of the track.

In one embodiment, the surface faces away from the axis of the rotator, and wherein the one or more ridges extend from the surface. In one embodiment, the distal end of the first sloped portion extends further from the axis than the proximal end of the first sloped portion. In one embodiment, at least part of the first sloped portion extends further from the axis than the surface of the track.

In one embodiment, the rotator comprises a second tongue extending in an opening in the surface in the track. This can provide a medicament delivery member guard lock at the end of an injection. In one embodiment, the second tongue extends in the axial direction from a proximal end to distal end, and wherein the distal end of the second tongue is attached to the tubular body and the proximal end of the second tongue is configured to flex relative to the surface of the track. In one embodiment, the second tongue extends in the axial direction from a proximal end to distal end, and wherein the proximal end of the second tongue is attached to the tubular body and the distal end of the second tongue is configured to flex relative to the surface of the track.

In one embodiment, the angle (A1) between the first sloped portion and the surface of the track is between 105 and 165 degrees, and wherein the angle (A2) between the second sloped portion and the surface of the track is between 105 and 165 degrees. In one embodiment, the surface of the tongue comprises a third sloped portion adjacent to the first sloped portion, wherein the third sloped portion is sloped towards the proximal end and is sloped in the circumferential direction relative to the axis.

In one embodiment, the pathway at the distal end of the track is aligned in the axial direction with only one of the two pathways at the proximal end of the track.

In one embodiment, the tongue is closer to the distal end of the rotator than to the proximal end of the rotator.

Another aspect of the present disclosure concerns a rotator for a medicament delivery device, the rotator comprising a tubular body extending from a proximal end to a distal end in an axial direction relative to an axis and in a circumferential direction around the axis, one or more ridges extending from a surface of the tubular body, the one or more ridges defining a track on a surface of the tubular body, the track extending in the axial direction from a distal end of the track to a proximal end of the track, the track comprising one pathway at the distal end of the track and two pathways at the proximal end of the track, wherein the two pathways at the proximal end of the track are separated by at least one of the one or more ridges, and a protrusion or tongue extending from the surface of the track, the protrusion or tongue extending in the axial direction from a distal end of the protrusion or tongue to a proximal end of the protrusion or tongue. In one embodiment, the protrusion or tongue is a tongue, and the proximal end of the tongue is attached to the rotator and wherein the distal end of the tongue is flexible in the radial direction relative to the axis.

Another aspect of the present disclosure concerns a rotator for a medicament delivery device, the rotator comprising a tubular body extending from a proximal end to a distal end in an axial direction relative to an axis and in a circumferential direction around the axis, one or more ridges extending from a surface of the tubular body, the one or more ridges defining a track on a surface of the tubular body, the track extending in the axial direction from a distal end of the track to a proximal end of the track, the track comprising one pathway at the distal end of the track and two pathways at the proximal end of the track, wherein the two pathways at the proximal end of the track are separated by at least one of the one or more ridges, a first tongue extending in an opening in the surface of the track, the first tongue extending in the axial direction from a first end to a second end, wherein the first tongue is attached to the tubular body at one end and is free to move in a radial direction relative to the tubular body at the other end, and a second tongue extending in an opening in the surface of the track, the second tongue extending in the axial direction from a first end to a second end, wherein the second tongue is attached to the tubular body at one end and is free to move in a radial direction relative to the tubular body at the other end.

Another aspect of the present disclosure concerns a medicament delivery device comprising any of the rotators described above. In one embodiment, the medicament delivery device comprises a housing extending from a proximal end to a distal end in the axial direction and extending in a circumferential direction around the axis and a medicament delivery member guard, wherein the rotator is in the housing, and wherein the rotator is able to move in the circumferential direction within the housing during use of the medicament delivery device, wherein the medicament delivery member guard is in the housing, and wherein the medicament delivery member guard is able to move in the axial direction within the housing during use of the medicament delivery device, and wherein the medicament delivery member guard comprises a protrusion, and the protrusion is arranged in the track of the rotator.

In one aspect, a feedback mechanism for a medicament delivery device is provided, comprising: a housing having a proximal end, a distal end, and extending along a longitudinal axis; a feedback element; a plunger rod associated to the housing and configured to be axially movable in relation to both the housing and the feedback element; a drive member configured to bias the plunger rod towards the proximal end of the housing and bias the feedback element towards the distal end of the housing; wherein the plunger rod comprises an interaction member configured to interact with the feedback element upon movement of the plunger rod in relation to both the housing and the feedback element for providing a feedback to a user of the medicament delivery device. This can provide a simple and reliable feedback mechanism for a medicament delivery device to indicate a delivery operation of the medicament delivery device.

According to one embodiment, the feedback is at least one of an audible feedback, a tactile feedback, visual feedback or an electronic feedback signal or the combination thereof.

According to one embodiment, the drive member can be a spring or a gas canister.

According to one embodiment, the interaction member comprises a tubular recess configured to force radial inwardly a resilient portion of the feedback element that extends through the tubular recess upon movement of the plunger rod in relation to both the housing and the feedback element.

According to one embodiment, the interaction member comprises a radial outwardly extending protrusion arranged on the outer surface of the plunger rod.

According to one embodiment, the feedback element comprises a longitudinally extending resilient arm; and wherein the radial outwardly extending protrusion is configured to flex a portion of the longitudinally extending resilient arm radially outwards upon movement of the plunger rod in relation to both the housing and the resilient feedback element.

According to one embodiment, the interaction member comprises a contact portion.

According to one embodiment, the feedback element comprises a longitudinal extending resilient arm having a counter contact portion; wherein the counter contact portion is configured to contact with the contact portion of the interaction member; such that the longitudinal extending resilient arm vibrates within the housing when a friction is created in between upon movement of the plunger rod in relation to the housing and the feedback element.

According to one embodiment, the feedback element is axially fixed to the housing.

According to one embodiment, the drive member is a drive spring; and wherein the feedback element comprises a guide member configured to radially support the drive spring.

According to one embodiment, the guide member comprises the resilient portion.

According to one embodiment, the feedback element comprises a retaining member, which is releasably connected to a counter retaining member of the housing.

According to one embodiment, the feedback element is arranged between the inner surface of the housing and the outer surface of the biased plunger rod; and wherein the retaining member is configured to release from the counter retaining member when the outer surface of the biased plunger rod is no longer in contact with the feedback element.

According to one embodiment, the feedback element is configured to be biased in relation to the housing upon releasement of the retaining member from the counter retaining member, such that the resilient feedback element is moved to interact with the housing whereby a second feedback is generated.

According to one embodiment, the second feedback is at least one of an audible feedback, a tactile feedback, visual feedback, an electronic feedback signal or a combination thereof.

These and other aspects of, and advantages with, the present disclosures will become apparent from the following detailed description of the present disclosure, the claims and from the accompanying drawings. Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which.

Like numbers shown in the figures refer to like elements throughout the description.

DETAILED DESCRIPTION

Figure 1:
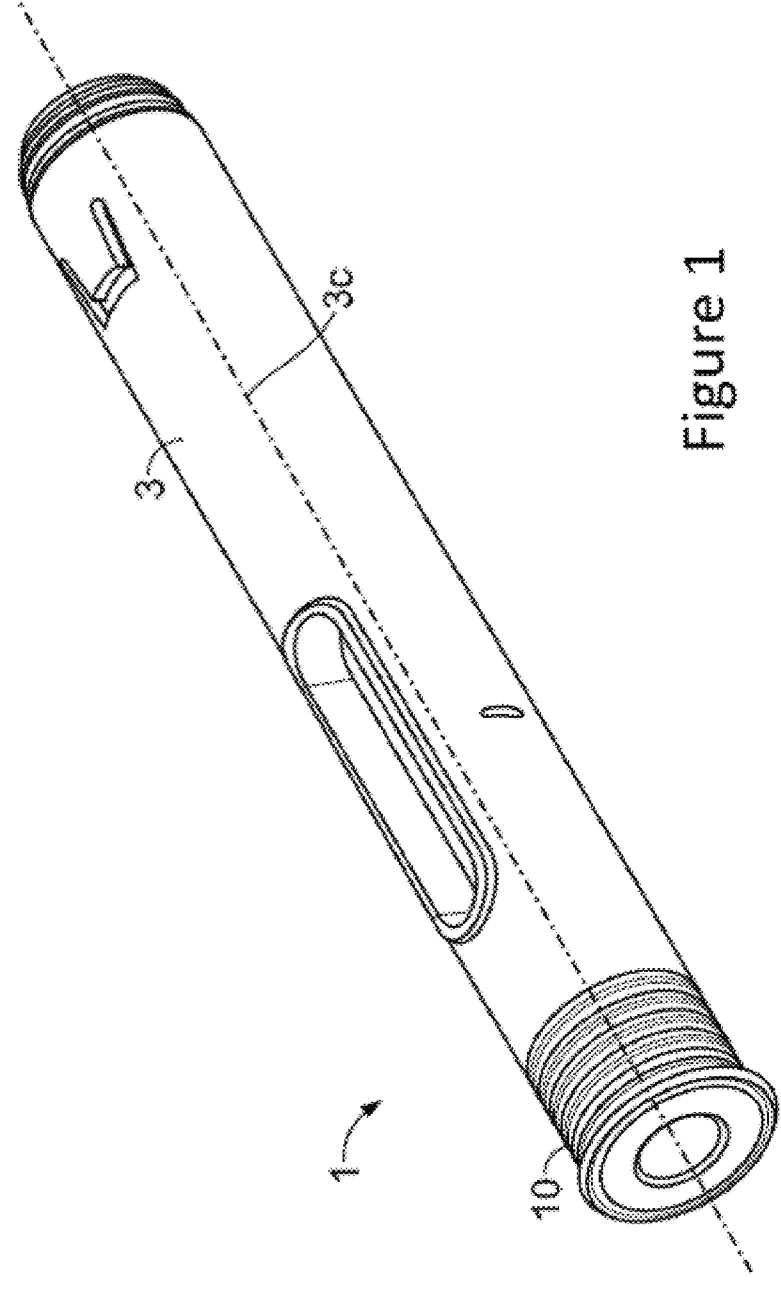
FIG. 1 is a perspective illustration of one possible complete medicament delivery device that can incorporate one or more of the feedback mechanisms of the present disclosure.

One part of the disclosure particularly describes feedback mechanisms incorporated in medical devices to provide information to a user relating to the start of medicament delivery. Specifically, in an injection device the feedback mechanism automatically indicates to a user through tactile or audible signals the beginning of the delivery of a set dose of medicament.

There are a vast number of medicament delivery devices on the market that are capable of performing any number of operations that benefit a user or patient. For example, there exist a variety of devices that automatically, semi-automatically or manually deliver one or more doses of medicament through injection (needle and needleless), inhalation, infusion, atomization, drops, patches, and implants. In each case there are a number of important device attributes that both patients and health care professionals find beneficial to know and monitor, for example, the activation of device prior to use, the beginning of the dose delivery process, cancellation or interruption of dose delivery, and the completion or end of the dose delivery process. In particular in an automatic medicament delivery device, such as an auto-injector, it is beneficial for the user of the device to receive an audible or tactile notification (feedback) that the medicament delivery process has begun. Receipt by the user of a start of medicament delivery notification can reduce or completely eliminate the possibility that a user interrupts or inadvertently stops the delivery process before completion.

Known medical devices are constructed with feedback mechanisms that signify the progress of medicament delivery and when the delivery sequence is completed; however, notification of the start of medicament delivery is not so well known. One known reference (WO 2017/140452) directed to an auto-injector does disclose notification of the initiation (commencement) of the drug delivery process. This disclosure involves a metal bracket that is caused to move distally inside the device to strike an inner surface of the auto-injector, thus providing a tactile or audible signal to the user.

With the need to monitor, collect and evaluate medical device attributes, especially in drug delivery devices, it is desirable to provide medical devices, such as medication delivery systems, that are economical to manufacture and that can automatically notify a user when the medicament delivery process commences. As such, it is an object of the present disclosure to provide medical devices that include a feedback mechanism that accurately notifies the user that the delivery process has begun. The disclosure presented below achieves this goal by providing a number of possible solutions for achieving automatic feedback signals indicative of the beginning of medicament delivery.

The present disclosure is applicable to a number of medical devices, including, but not limited to, devices that automatically, semi-automatically or manually deliver one or more doses of medicament through injection (needle and needleless), inhalation, infusion, atomization, drops, patches, and implants. Incorporating one or more automatic feedback mechanisms into these medical devices ensures that the user of the device will be notified of the beginning of the medicament delivery sequence.

As indicated, an automatic feedback mechanism for a medicament delivery device, and a medicament delivery device incorporating such an automatic feedback mechanism, will now be described.

As evident from above summary, the feedback mechanism of the present disclosure may be embodied in many different forms and should not be construed as limited to just the embodiments set forth herein; rather, these embodiments are provided by way of example so that this disclosure will be thorough and complete, and will fully convey the scope of the feedback mechanism to those skilled in the art.

Although the medical device described below is a medicament delivery device configured as a disposable single-use, pen-type injector, such as an auto-injector, any type of single use automatic medicament delivery device could incorporate the feedback mechanisms of the present disclosure, including, but not limited to, inhalers or eye dispensers. Likewise, the medical device may be a training device that replicates a medicament delivery device.

Figure 2:
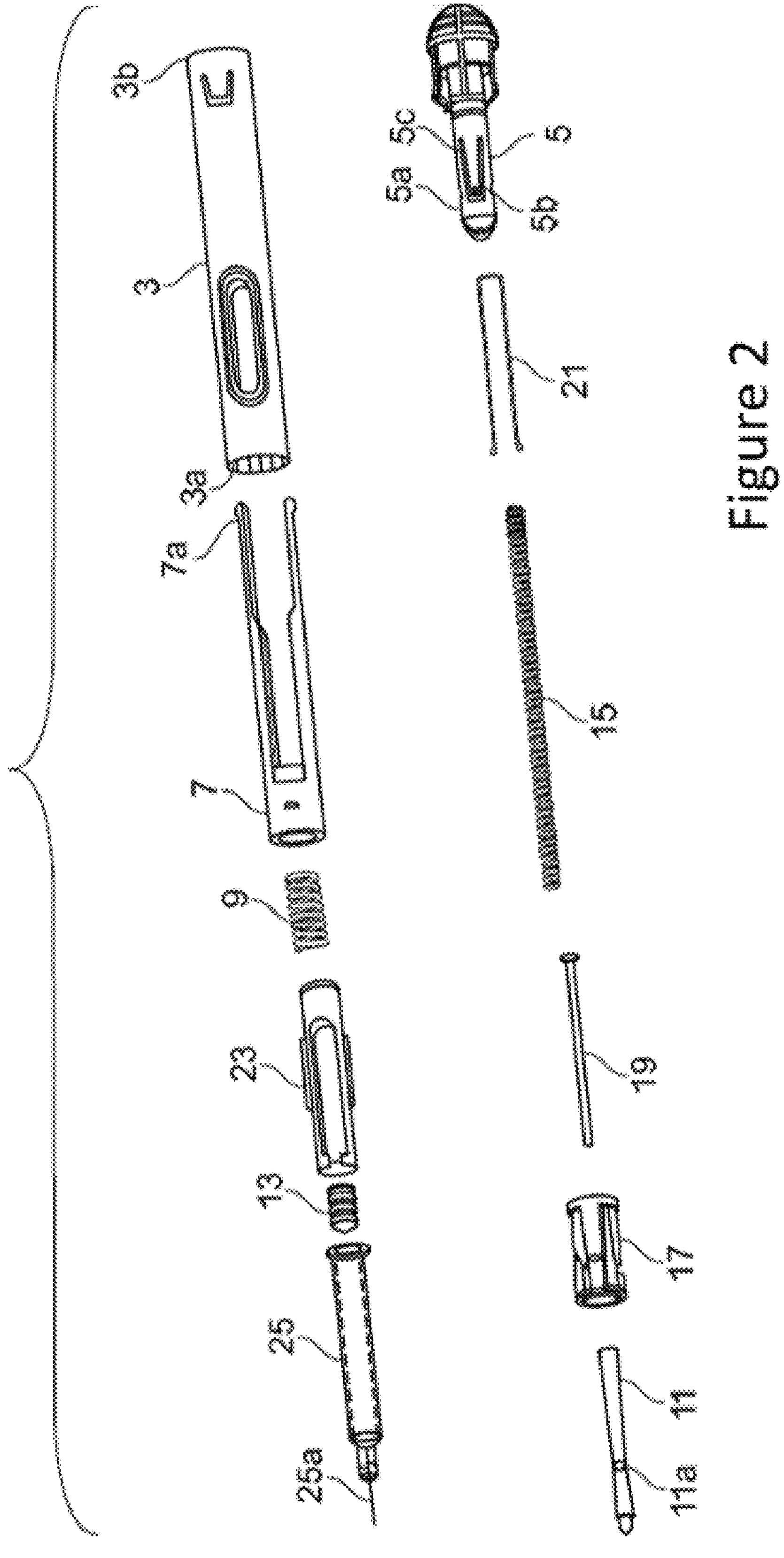
FIG. 2 illustrates an exploded view of the medicament delivery device in FIG. 1.

One example of a medical device that can have one or more of the start of delivery feedback mechanisms is the pen-type auto-injector 1 shown in FIG. 1. The complete injection device 1 is illustrated and an exploded view of the device is shown in FIG. 2.

The auto-injector as described in more detail below has a housing 3 having a proximal end and a distal end, a plunger rod received by the housing and axially displaceable from an initial position to a final position relative to the housing, and a rear cap having a tubular housing. The rear cap is received into an open distal end of the housing and is rotationally fixed relative to the housing. The tubular housing is arranged to receive the plunger rod and can have an end of dose delivery signal generating member received inside, where the plunger rod is arranged to be received by the signal generating member. A first energy accumulation member is arranged inside the hollow plunger rod to bias the plunger rod in a proximal direction towards the proximal end of the housing and to bias the signal generating member in a distal direction which is opposite to the proximal direction.

In an initial position, the plunger rod is in a pre-tensioned state and is arranged to flex or press the proximal ends of the signal generating member radially outward towards the tubular housing of the rear cap thereby engaging the signal generating member with the tubular housing and retaining the distally biased signal generating member in a fixed axial position relative to the housing. In this axial position, the signal generating member is distanced from the distal inner surface of the rear cap.

Prior to use, the plunger rod is arranged axially fixed in its initial position. When the medicament delivery device is activated, i.e., when a user initiates medicament delivery, the plunger rod is released from the initial position and is pressed in the proximal direction by the first energy accumulation member. When the plunger rod has been displaced a distance corresponding to a distance signifying the end of dose delivery the contact between the plunger rod and the signal generating member will cease and the signal generating member will be allowed to flex radially inwards towards its radially unbiased state. The signal generating member will thereby disengage from the tubular housing. Because the signal generating member is biased in the distal direction by the first energy accumulation member, the end of dose delivery signal delivery member will be thrown towards the distal inner surface of the rear cap. This results in an audible “click” sound, and also provides the user with a tactile sensation. Although the end of dose delivery notification feature is optional, as described below, the auto-injector will contain a start of dose delivery feedback mechanism.

The auto-injector described herein also contains a medicament delivery member, for example an injection needle, a needle cover received by and rotationally fixed with respect to the housing, and a rotator arranged to receive the plunger rod and the tubular housing of the rear cap. The needle cover is displaceable axially between an extended position and a retracted position relative to the proximal end of the housing. The needle cover is biased towards the extended position by a second biasing member. The rotator is arranged to interact with the needle cover, and has a guide structure arranged to convert linear or axial motion in the distal direction of the needle cover to rotational motion of the rotator relative to the housing and the tubular housing that is positioned in a cantilevered fashion within the housing and that is parallel to the longitudinal axis of the housing.

As stated, FIG. 1 shows an example of an auto-injector device 1 designed and configured for automatically injecting a fixed dose of medicament from a container 25 of medicament positioned with housing 3 through a needle 25*a*. The auto-injector can be configured as a single use, disposable device. The housing 3 has a proximal end 3*a*, a distal end 3*b*, and a longitudinal axis 3*c*. Such a device is typically provided with cap 10 that, when attached, maintains the medicament delivery member 25*a*, for example a needle (see FIG. 2), in a sterile condition. The device also has a rear cap 5 having a tubular housing 5*a* and a flexible arm 5*b* position on or integral with the tubular housing. Preferably, the flexible arm 5*b* is formed as part of a cut-out 5*c* in the tubular housing. The rear cap 5 can be a unitary member that is mounted to the distal end 3*b* of the housing 3 such that the rear cap and its proximally projecting tubular housing 5*a* is rotationally fixed relative to the housing. The device further includes a needle cover 7 arranged to be slidably received inside the housing 3 such that it can only move axially, and is arranged to be biased in the proximal direction by the second biasing or resilient or energy accumulation member 9.

As the exploded view of FIG. 2 depicts, the medicament delivery device 1 further includes a hollow plunger rod 11 which is arranged to be biased towards the proximal end 3*a* by a first biasing or resilient member or energy accumulation member 15. A medicament container 25, preferably a pre-filled syringe, contains a plunger or piston 13 and has an attached needle 25*a*, preferably a staked injection needle. The plunger rod 11 abuts plunger 13 inside the barrel of the medicament container 25 and is biased in the proximal direction by the first energy accumulation member 15, which can be a spring. Likewise, the second resilient member or energy accumulation member 9 can also be a spring arranged to bias the needle cover 7 in the proximal direction.

The rotator 17 is configured and designed to receive the plunger rod 11, the first energy accumulation member 15, rod 19, the end of medicament delivery signal generating member 21, and the tubular housing 5*a* of rear cap 5. The signal generating member 21 is preferably a U-shaped metal bracket. The auto-injector further contains a medicament container holder 23. The hollow plunger 13 is arranged to move during dose delivery axially in the proximal direction relative to the medicament container 25 by linear displacement of the plunger rod 11 to thereby expel medicament through the needle 25*a*.

According to the present example, the plunger rod 11 has a radial opening 11*a*, and the tubular housing 5*a* which is arranged to receive the plunger rod 11 has a corresponding flexible arm 5*b* that is designed to flex in a radial direction so that it can engage and disengage with the opening 11*a*. When the rotator 17 is in a first position the flexible arm 5*b* is engaged with the plunger rod such that the plunger rod is held axially fixed relative to housing 3 and tubular housing 5*a*. Rotation of the rotator 17 to second position causes the flexible arm 5*b* to flex radially away from the longitudinal axis 3*c*, thus disengaging the flexible arm from opening 11*a*. This disengagement causes the first energy accumulation member 15 to release a proximally directed force upon the inside of the plunger rod driving it axially in the proximal direction whereby it pushes plunger 13 in same direction causing the medicament in container 25 to start expelling from needle 25*a*.

Figure 3:
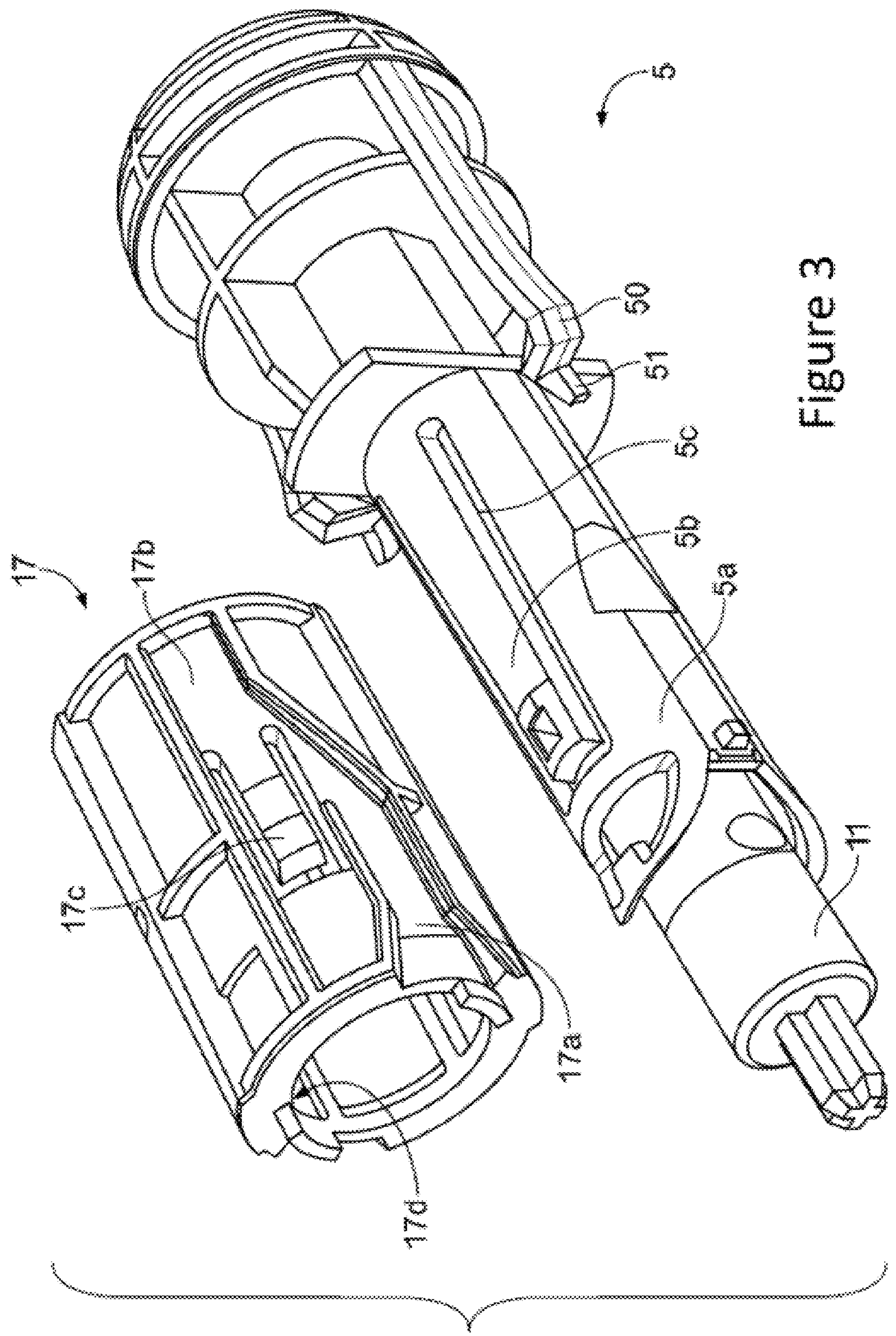
FIG. 3 illustrates a perspective view of the rear cap and the rotator of the feedback mechanism of the present disclosure.

Rotation of the rotator 17 from the first position to the second position is caused when the proximal end of the needle cover 7 is pushed against an injection site by a user of the device. This causes the needle cover 7 to slide axially in the distal direction relative to the housing 3 whereby the proximal ends 7*a* of the needle cover move within channel 17*a* located on the outside surface of the rotator 17 (see FIG. 3). As the needle cover moves further axially in the proximal direction, the distal ends 7*a* engage the sides of channel 17*a* causing the rotator 17 to rotate such that the distal ends 7*a* move into channel 17*b*. Prior to rotation of the rotator, the inside surface 17*d* of the rotator prevents flexible arm 5*b* from flexing radial outward relative to the cut-out 5*c* and the plunger rod 11 thus maintaining engagement with the plunger rod to prevent axial movement in the proximal direction. When the rotator 17 is rotated from the first position, the inner structure of the tubular rotator 17 is designed such that it will provide less radial force on the flexible arm 5*b*, allowing the flexible arm 5*b* to flex radially outwards and to disengage from the plunger rod 11. The plunger rod 11, which is biased in the proximal direction, is thereby displaced axially and medicament administration is thus commenced as the plunger rod 11 pushes the plunger 13 inside the medicament container 25.

Completion of the medicament delivery and removal of the proximal end of the needle guard from the injection site will cause the needle cover to move proximally as a result of the second resilient member 9. This axial and proximal movement of the needle cover 7 will cause distal ends 7*a* to move proximally in channel 17*b* and will engage with lock 17*c*. Once locked, the needle cover will no longer move distally relative to the housing and will be in a locked extended position such that it covers the needle 25*a*, thus preventing accidental needle sticks.

The start of dose delivery notification features or the feedback mechanisms that are disclosed herein involve the interaction of the rotator 17 with the rear cap 5 and/or with an inside surface 3*d* (see FIG. 6) of housing 3. Specific embodiments are shown in FIGS. 4 to 7 and are described in detail below. These feedback mechanisms are each arranged to notify a user of a start of the expulsion of medicament from the medicament container 25.

Figure 4:
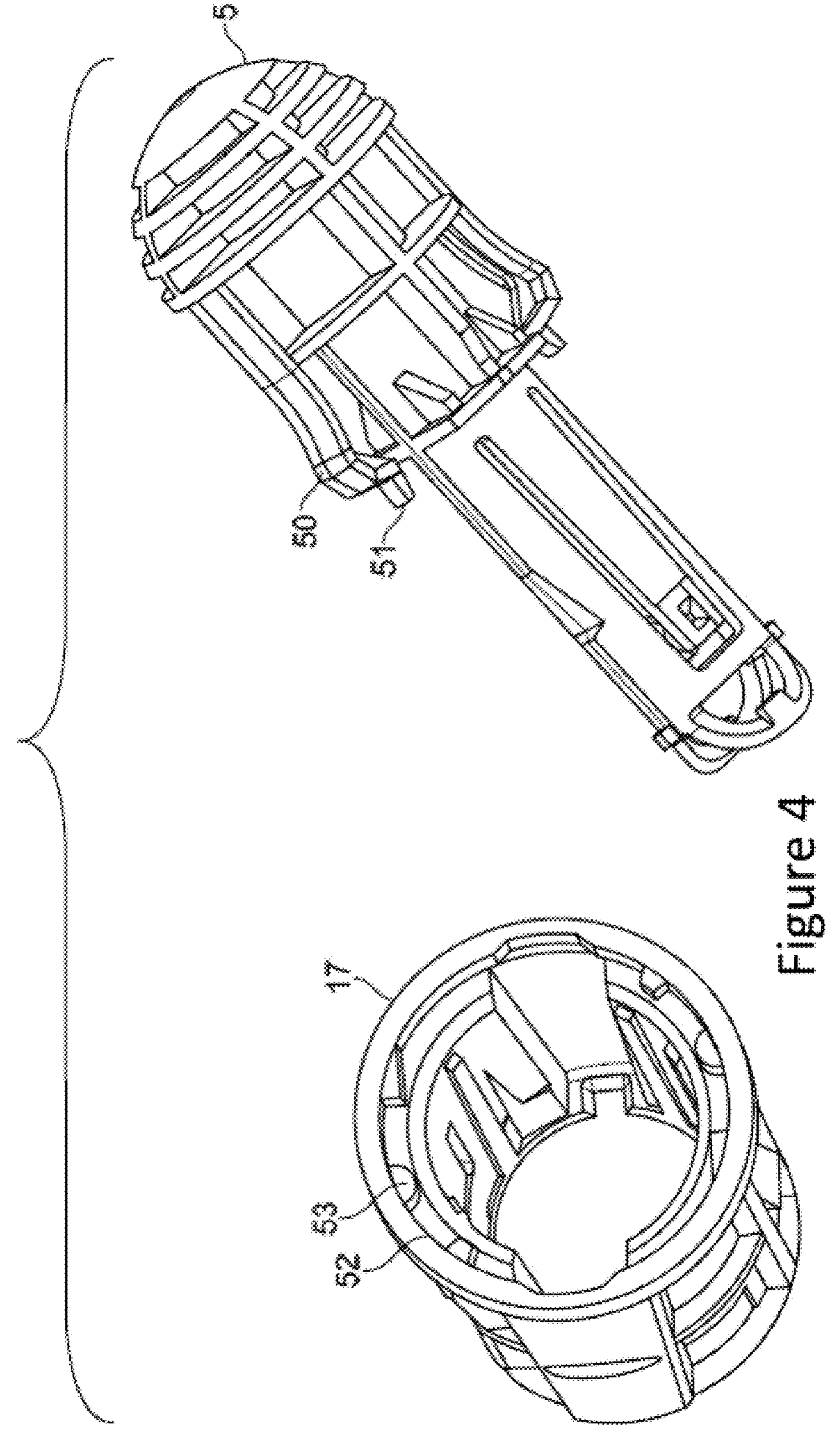
FIG. 4 illustrates a perspective view of the rear cap and the rotator of one possible embodiment of the feedback mechanism of the present disclosure.

Starting with a first embodiment, as illustrated in FIG. 4, the start of medicament delivery mechanism involves the interaction of the rear cap 5 with an inside surface 52 of the rotator 17. Specifically, a flexible finger 50 which projects proximally from the distal end of the rear cap 5 will interact with an inward directed protrusion 53 that engages the flexible finger 50 as the rotator 17 moves from the first position to the second position such that a proximal end or hook 51 of the finger 50 will strike the inside surface 52 of rotator 17 causing an audible or tactile feedback once the rotator has reached the second position. The proximal end of the flexible finger 50 is normally biased radially outward. As the rotator turns relative to the finger 50, the engagement with the inward directed protrusion 53 flexes or bends finger 50 such that it is now biased radially inward in direction that is generally transverse to the longitudinal axis 3*c*. As the hook 51 contacts the side of the protrusion it will slide along the outer surface of the protrusion similar to how a follower engages the surface of a cam. The hook 51 will continue to engage the surface of the protrusion 53, essentially following a path that traces and defines a portion of the shape of the protrusion. This path can be described as the hook 51 climbing up and over protrusion 53. As the hook 51 reaches the apex of the protrusion 53, the hook 51 reach its maximum deflection radially inward that will load the hook 51 with a radial deflection force. After reaching this maximum deflection point, the hook 51 then will momentarily disengage from the surface of the protrusion 53 and the radial deflection force will cause the hook 51 to flex back radially outward in the opposite direction, i.e., it will snap back, until hook 51 strikes either the surface of protrusion 53 or the inside surface 52. This striking of the hook 51 with the rotator results in in the audible or tactile feedback notification that the medicament delivery has begun.

Figures 5A, 5B, 5C:
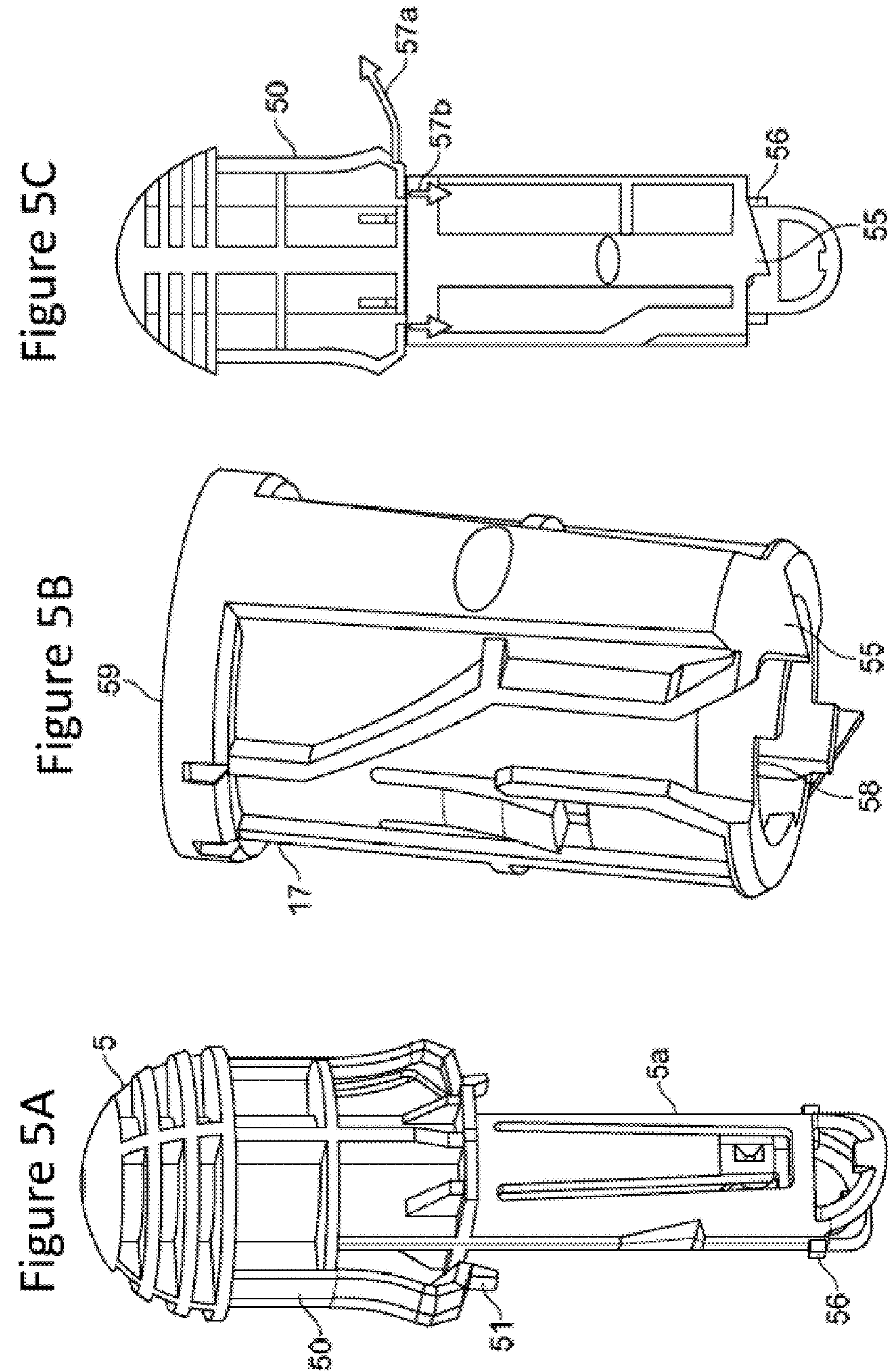
FIG. 5 illustrates views of the rear cap and the rotator of second possible embodiment of the feedback mechanism of the present disclosure.

FIG. 5 illustrates another embodiment of the start of medicament delivery mechanism which involves the interaction of the terminal proximal end face 58 of the rotator 17 with one or more blocks 56 projecting radially outward from the proximal end of the tubular housing 5*a* of rear cap 5. The terminal proximal end face 58 of the rotator 17 includes one or more ramped surfaces 55. The ramped surfaces are generally triangular or wedge shaped and are proximally directed from the proximal terminal end face 58. The ramped surface 55 is positioned on the terminal end face 58 so that an angled side, i.e., a ramp, of the ramped surface 55 such that the block 56 will first contact (engage) the bottom of the ramp that is essentially in line and level with terminal proximal end face 58. As the rotator is rotated by the axial movement of the needle cover 7 during activation of the device, the angled side of the ramped surface 55 engages block 56, i.e., similar to how a follower engages and slides along the surface of a cam. As the rotator rotates relative to the stationery rear cap 5 and its tubular housing 5*a*, the block 56 will slide along the surface of the angled side of the ramped surface 55 essentially following an angled path that traces and defines a portion of the shape of the ramped surface 55. Stated differently, the angled side and the block will be in sliding engagement such that they move relative to each other causing the block to move up the angled side of the generally triangular shaped ramped surface 55. This sliding engagement between the block 56 and the angled side of the ramped surface 55 can be described as the block 56 "climbing up" angled side of the ramped surface 55 even though it is the ramped surface 55 that moves (rotates) relative to the block 56, which is rotationally fixed relative to the device housing.

As the block 56 reaches the end of the angled side of the ramped surface 55, the rotator 17 will have then been forced in a maximum axial distance in the distal direction. After reaching this maximum axial distance, further rotation of the rotator 17 will cause disengagement of the block 56 from the angled side of the ramped surface 55. This disengagement of the block 56 will cause the rotator 17 to move axially back in the opposite (or proximal) direction, i.e., it will "snap back", such that block 56 strikes either a second side of the ramped the surface of protrusion 53 or the terminal end face 58. This striking of the block 56 with the rotator results in in the audible or tactile feedback notification that the medicament delivery has begun.

As the angled side of the ramped surface 55 rotates relative to the rear cap 5, there will be a sliding engagement with the block 56 such that the rotator 17 to be forced (pushed) in the distal direction, which causes the fingers 50 to bow radially outward as indicated by directional arrow 57*a*. This in turn generates a force 57*b* in the proximal direction against the terminal distal end face 59 of the rotator. Hook 51 at the proximal end of the finger 50 transmits the biasing force 57*b* to the rotator. The relative movement of the angled side of the ramped surface 55 and the block 56 can be described as the block 56 "sliding up" the angled side of the ramped surface 55. As the block slides (or rides) higher up the angled side, a greater force 57*b* is generated as the fingers 50 continue to bow. The ramped surface 55 and angle (or height) of the angled side is designed and positioned at the end face 58 of the rotator so that when the rotator has completed the rotation from the first to the second position, the block 56 has arrived at the end of the angled side of the ramped surface and then disengages from the angled side. i.e., "falls off" the angled side, resulting in the generation of the start of medicament delivery feedback signal, which can be audible or tactile, as described above. The force 57*b* drives the rotator proximally after disengagement of the ramped surface from the block causing the proximal end surface 58 to strike the block 56 and to generate the feedback signal.

Figures 6A, 6B, 6C, 6D:
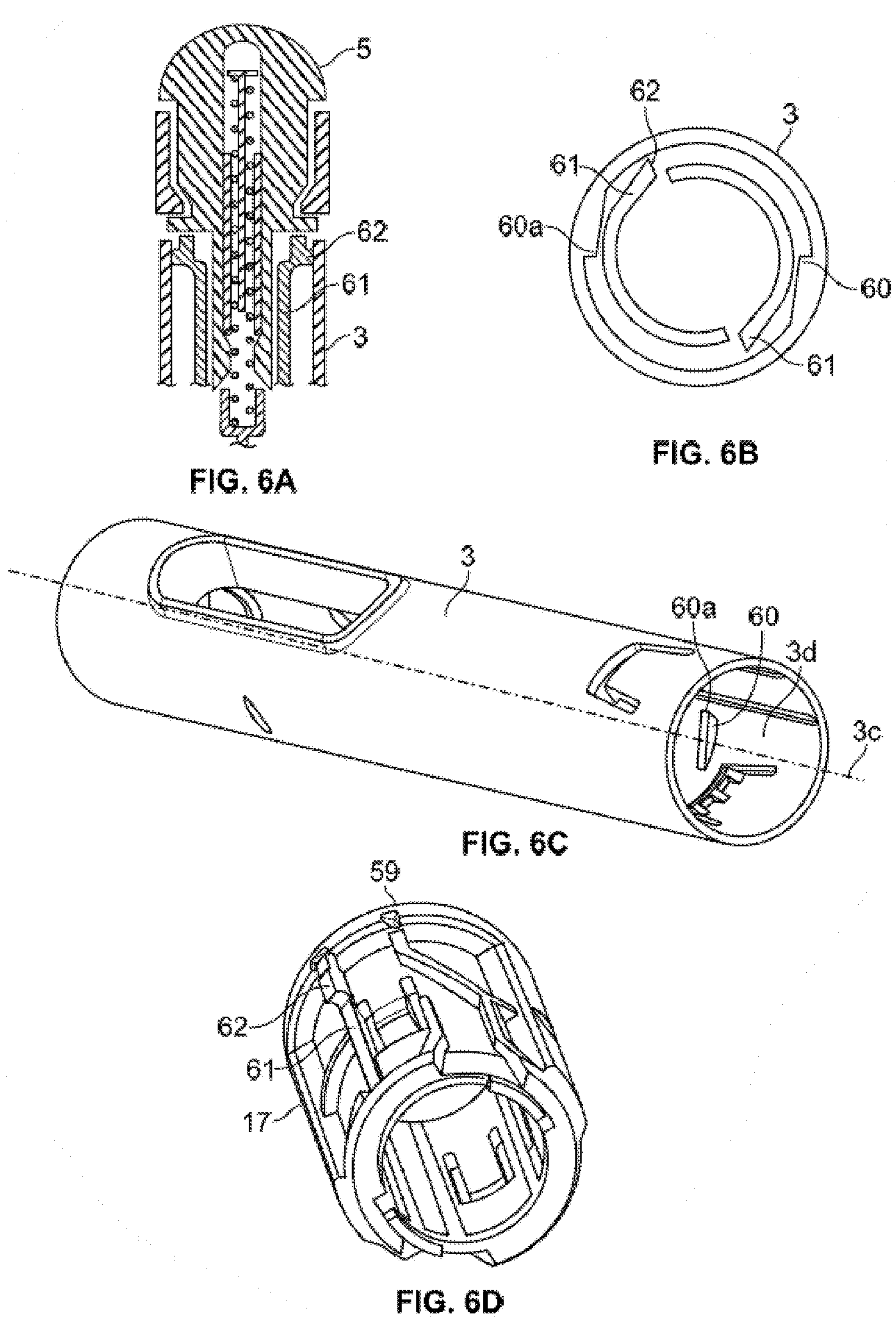
FIG. 6 illustrates views of the rear cap and the rotator of third possible embodiment of the feedback mechanism of the present disclosure.

FIG. 6 illustrates yet another embodiment of the start of medicament delivery mechanism that involves the interaction of the inside surface 3*d* of housing 3 and a flexible lever 61 located on an outside surface of rotator 17. Although FIG. 6 illustrates that the flexible lever 61 is arranged parallel to the longitudinal axis 3*c*, the flexible lever could alternatively be positioned on the rotator outer surface such that it is transverse to the axis. Rotation of the rotator 17 from the first position to the second position causes an outwardly projecting knob 62 located at the end of the flexible lever 61 to engage an angled side of ramp 60 positioned on the inside surface 3*d* of the housing 3. This ramp 60 can be generally triangular or wedge shaped and integral with the housing, such as through co-molding, or it could be a separate component that is attached, e.g., glued or welded, to the inside of the housing. The angled side of ramp 60 is positioned relative to the inside surface 3*d* of the housing 3 such that the knob 62 will first contact the lowest portion of the angled side, i.e., the bottom of the ramp, that is essentially in line and level with inside surface 3*d*. During activation of the injector, which is caused by the axial distal movement of the needle cover 7, the rotator is rotated from the first position to the second position. The configuration and orientation of the ramp 60 and of the flexible lever 61/knob 62 is designed such that during the rotation of the rotator the knob 62 will engage the angled side of the ramp 60 and will slide up, i.e., "ride along", the ramp 60, which causes the flexible lever 61 to be flexed radially inward relative to axis 3*c*, thus loading the lever 61 with a radial force biased radially outward. The sliding engagement of the knob 62 with the angled side of ramp 60 is similar to how a follower engages and slides along the surface of a cam. When the rotator reaches the second position, the knob will have reached the end of the angled side of ramp 60 and will then disengage from ramp 60, i.e., it will "drop off" the edge 60*a* of the ramp 60, causing the flexible lever 61 to spring back radially which in turn causes the knob 62 to strike the inside surface 3*d* of the housing. This strike generates the start of medicament delivery feedback signal, which can be audible or tactile signifying the rotator has reached the second position and medicament expulsion has begun.

Figures 7A, 7B, 7C, 7D, 7E, 7F:
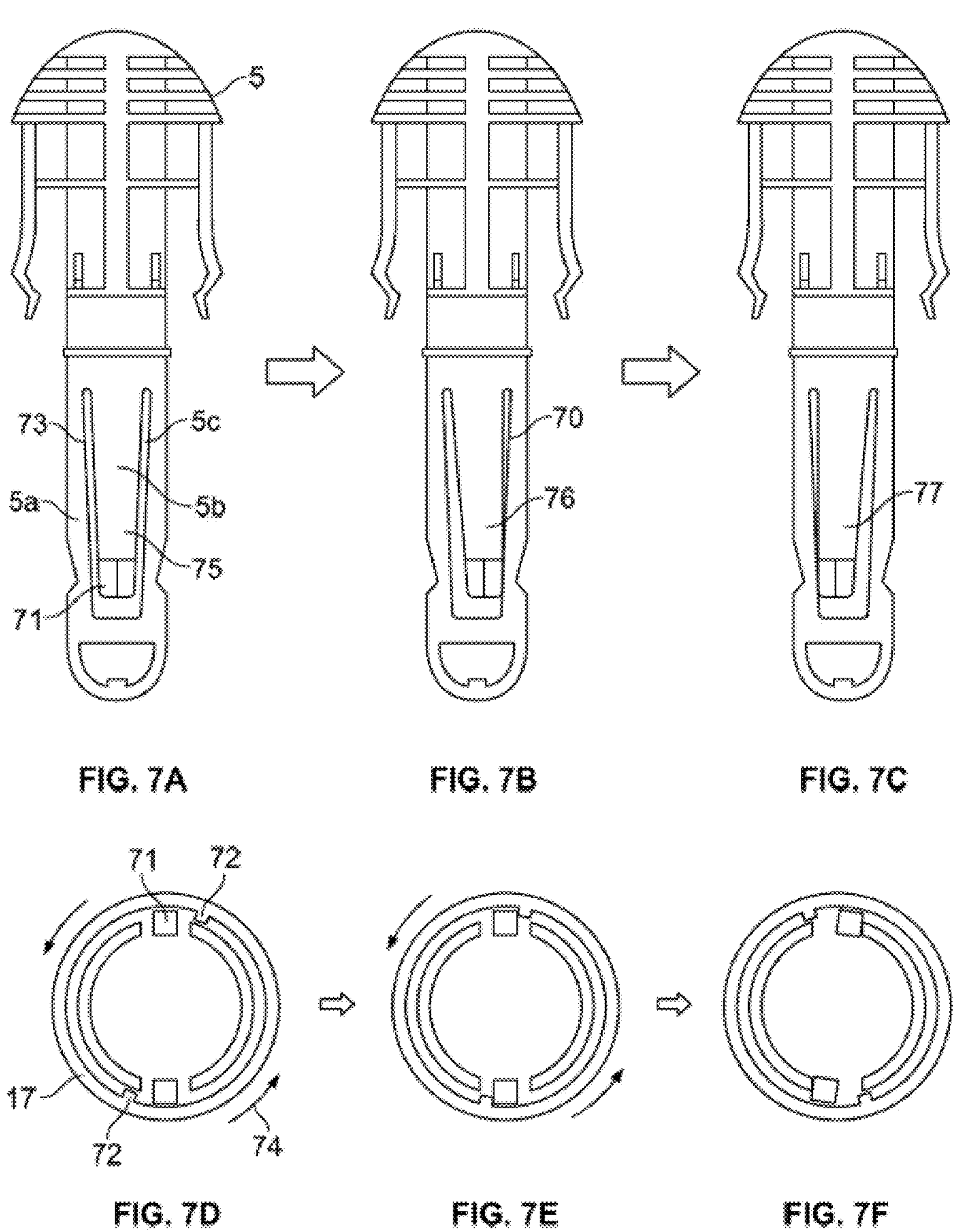
FIG. 7 illustrates progressive views of the rear cap and the rotator of fourth possible embodiment of the feedback mechanism of the present disclosure

FIG. 7 illustrates a fourth embodiment of the start of medicament delivery mechanism of the present disclosure that involves the interaction of the rotator 17 with the flexible arm 5*b* of the tubular housing 5*a*. More specifically, the rotator 17 has an inwardly directed nib 72 that engages the flexible arm 5*b* when the rotator rotates from the first to the second position. This engagement can be between the nib 72 and an outer protrusion 71 directed radially outward that is located on the proximal end of the flexible arm. As the rotator 17 is rotated in direction 74 relative to the tubular housing 5*a* during activation of the injector, the engagement of the nib 72 with the flexible arm 5*b* causes the flexible arm to move transversely relative to the longitudinal axis 3*c* such that an audible or tactile feedback is emitted once the rotator has reached the second position. FIG. 7 illustrates the three states or positions of the flexible arm, namely 75, 76 and 77. The movement of the flexible arm from the first state 75, where the flexible arm is in a generally neutral or non-biased position, roughly centered in cut-out 5*c*, to the second state 76, where the flexible arm is cocked or loaded in a direction that places it generally adjacent the side wall 70 of cut-out 5*c*, to the third state 77, where the flexible arm has unloaded and has swung back past the first state 75 such that it strikes side wall 73 to generate the start of medicament delivery feedback, which can be audible or tactile. This signifies that the rotator has reached the second position and medicament expulsion has begun.

The design and configuration of the nib 72 and the outer protrusion 71 of the flexible arm is such that the nib and protrusion will interact to form a releasable engagement that will be sufficient to allow the moving nib to cock or flex the flexible arm transversely during the rotation of the rotator as it moves from the first position to the second position. Upon arriving at the second position, the nib 72 will disengage from the protrusion 71 and thus release the flexible arm 5*b* to allow it to flex in the opposite transverse direction where it will then strike side wall 73 and will emit the feedback notification. Preferably, the flexible arm is designed and configured with a taper such that the proximal end of the flexible arm where it connects or extends from the tubular housing 5*a* and has a smaller width than the distal end which free floats within cut-out 5*c*.

The above-presented description and figures are intended by way of example only and are not intended to limit the present disclosure in any way except as set forth in the following claims. It is particularly noted that persons skilled in the art can readily combine the various technical aspects of the various elements of the various exemplary embodiments that have been described above in numerous other ways, all of which are considered to be within the scope of the disclosure.

Another part of the disclosure focusses on rotators for medicament delivery devices.

Figures 8, 9:
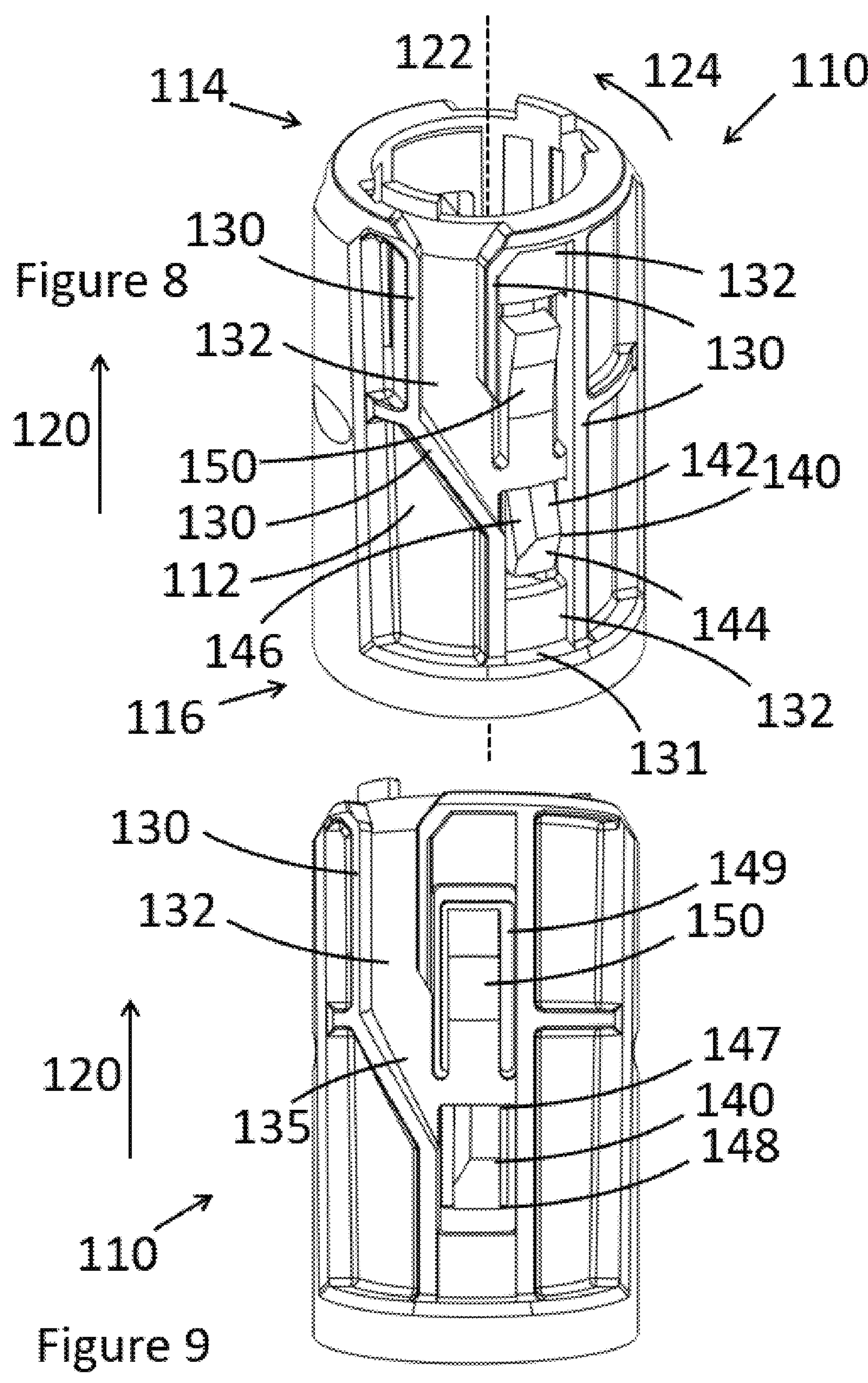
FIG. 8 shows a perspective view of an example rotator.
FIG. 9 shows a side view of the rotator of FIG. 8.

FIGS. 8 and 9 show a perspective view of an example of a rotator 110 for a medicament delivery device according to the present disclosure. The rotator 110 comprises a tubular body 112 extending from a proximal end 114 to a distal end 116 in an axial direction 120. Ridges 130 extend from a surface of the tubular body 112, with the ridges 130 defining a track (labyrinth) 132 on the surface of the tubular body 112, the track 132 extending in the axial direction 120 from a distal end of the track 132 to a proximal end of the track 132. The track 132 comprises one pathway 136 at the distal end of the track 132 and two pathways 134, 138 at the proximal end of the track 132. The typical shape of the pathways will be described in more detail with reference to another similar example shown in FIG. 10. The two pathways 134, 138 at the proximal end of the track 132 are separated by a part of the ridge 130. In the example in FIG. 10, a tongue 140 extends in an opening 139 in the surface in the track 132 and is configured to flex relative to the surface of the track 132. The tongue 140 (and particularly a protrusion 141 of the tongue; see FIG. 12 for example) comprises a surface extending in the track 132. The surface of the tongue comprises a first sloped portion 142 and a second sloped portion 144. The second sloped portion 144 is closer to the distal end 116 of the tubular body 112 than the first sloped portion 142. The first sloped portion 142 and the second sloped portion 144 are angled relative to the surface of the track 132, with the first sloped portion 142 angled towards the proximal end 114 of the tubular body 112 and the second sloped portion 144 angled towards the distal end 116 of the tubular body 112.

An optional third sloped portion 146 of surface of the tongue 140 can also be seen in FIGS. 8 and 9. An optional second tongue 150 is also shown in a second opening 149 in the surface of the track 132 in FIGS. 8 and 9. The structure and purpose of the third sloped portion 146 and the second tongue 150 is described in more detail below.

Figures 12, 13:
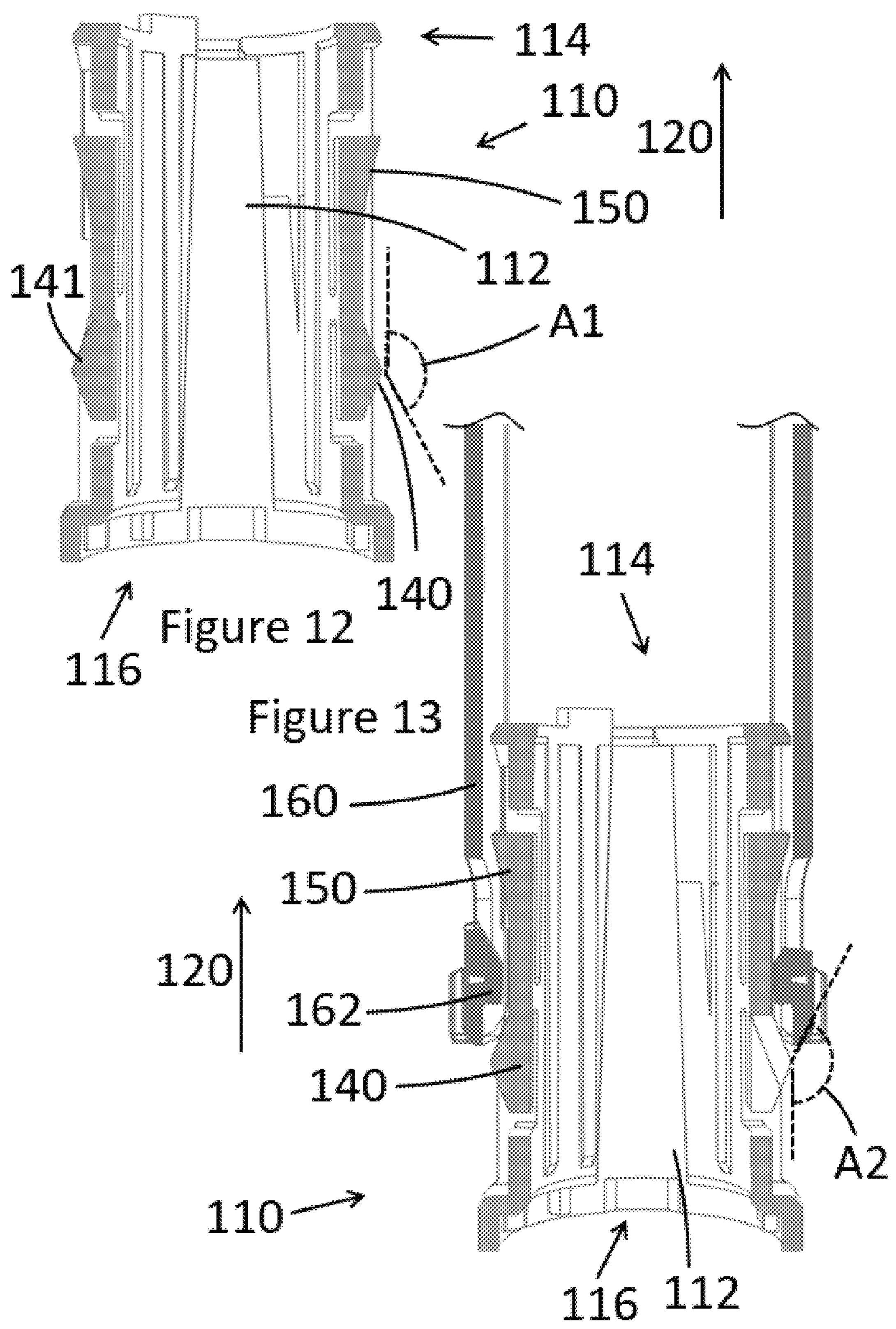
FIG. 12 shows a cross-sectional view of the rotator in FIG. 8.
FIG. 13 shows a cross-sectional view of the rotator in FIG. 8, along with a corresponding medicament delivery member guard.

In FIGS. 12 and 13, a further view of the rotator 110 of FIGS. 8 and 9 can be seen. In FIG. 13, a medicament delivery member guard 160 is also shown, with a protrusion 162 of the medicament delivery member guard 160 shown in the track 132. As can be seen in FIGS. 12 and 13 in particular, a protrusion 141 of the tongue 140 of the rotator 110 is aligned to engage with the protrusion 162 of the medicament delivery member guard 160 during use, as described in more detail below.

The rotator described above is typically a standalone component in a medicament delivery device. An example of a type of medicament delivery device the rotator could be used in is described in WO 2011/123024, which is herein incorporated by reference, particularly with reference to FIGS. 8 and 9 and the corresponding description. Briefly, a medicament delivery device incorporating the rotator would comprise a housing (such as an outer housing), a medicament delivery member guard and the rotator. The rotator is able to move rotationally (in the circumferential direction) within the housing during use of the medicament delivery device. The medicament delivery member guard is able to move in the axial direction within the housing during use of the medicament delivery device. Typically, axial movement of the rotator relative to the housing would be restricted. Typically, rotational movement of the medicament delivery member guard relative to the housing would be restricted. The medicament delivery device also typically comprises a powerpack inside the housing, the powerpack comprising the rotator and a plunger rod, a medicament barrel inside the outer housing and a cap. The medicament barrel typically comprises a medicament container and a medicament delivery member such as a needle.

Figures 10, 11:
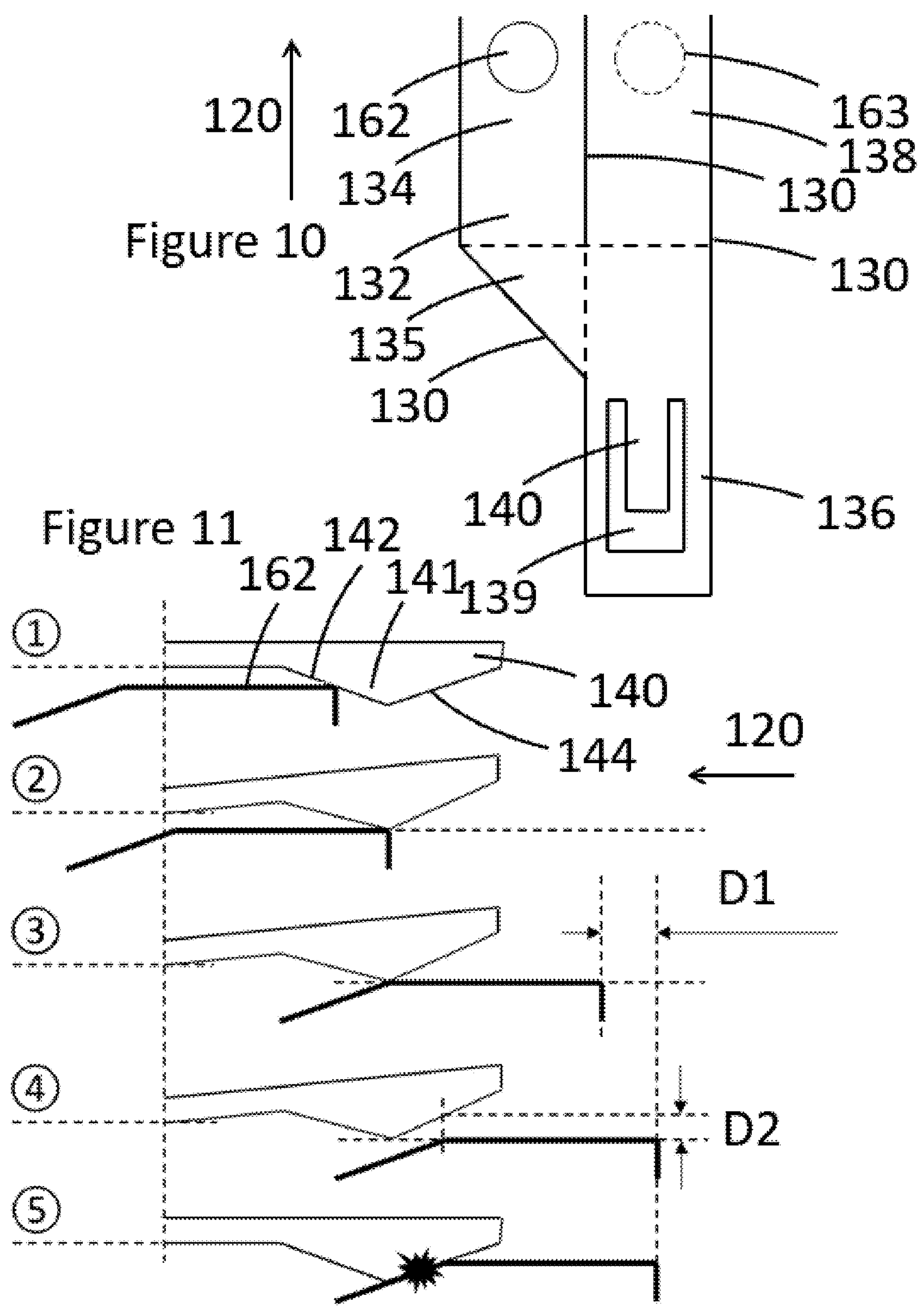
FIG. 10 shows a simplified line diagram of another example of the track of a rotator.
FIG. 11 shows a stylised cross-sectional side view of the interaction of a tongue and a protrusion of a medicament delivery member guard at various stages in an injection, to show an example of how the described features can cause a click.

In a medicament delivery device comprising the rotator 110 and the medicament delivery member guard 160, the rotator 110 and medicament delivery member guard 160 can move relative to one another. The typical movement of the rotator relative to the medicament delivery member guard will now be described with reference to FIGS. 10 and 11. FIG. 10 shows a simplified view of another example track 132, where the main difference between the example in FIG. 8 and the example in FIG. 10 is the location of the tongue. FIG. 11 shows a simplified view of the interaction between another similar example of a protrusion 162 and a tongue 140. As mentioned above, the track 132 can be thought of as a combination of three separate pathways, namely a first pathway 134, a second pathway 136 and a third pathway 138, which are shown separated by dotted lines in FIG. 10. A transition portion 135 is considered to be part of the first pathway 134.

The first and third pathways 134, 138 typically correspond to the two pathways at the proximal end of the track as described above, and the second pathway typically corresponds to the pathway at the distal end of the track as described above. The protrusion 162 will be described as 'following' the track/pathways, which in practice means that the protrusion is restricted to movement along the track/pathways by the ridges 130, and is either touching or near to the surface of the tubular body in the track as a result.

The transition portion 135 is a portion in which the width of the first pathway is narrower in the circumferential direction, with the transition portion tapering (reducing) in width towards the distal end of the rotator. This transition portion is designed to guide the protrusion 162, and it is normally this portion that results in the rotation of the rotator, which is described in more detail below.

The protrusion 162 of the medicament delivery member guard 160 would initially be at the position shown in FIG. 10 in an assembled and unused medicament delivery device. When an injection is carried out using the medicament delivery device, the medicament delivery member guard moves in the distal direction relative to other parts of the device (relative to the rotator and relative to an outer housing, for example). In other words, relative to the medicament recipient, the medicament delivery member guard remains stationary with the proximal end of the medicament delivery member guard against the dose delivery site while the other parts of the device move in the proximal direction towards the dose delivery site. As the medicament delivery member guard moves relative to the rotator, the protrusion 162 also moves relative to the rotator and is arranged in the track so that it follows the track, firstly along the first pathway and then along the second pathway. The medicament delivery member guard is typically rotationally fixed relative to other parts of the medicament delivery device (e.g. an outer housing, which will be used here as an example). During the initial movement of the protrusion in the first pathway, the medicament delivery member guard moves axially relative to the outer housing and the rotator remains stationary relative to the outer housing. As the protrusion enters the transition portion 135 and transfers to the second pathway 136, the medicament delivery member guard continues to move axially relative to the outer housing, and the rotator also rotates (in the circumferential direction) relative to the outer housing and the medicament delivery member guard. The protrusion 162 also interacts with the tongue 140 at this stage; this interaction will be described in more detail below with reference to FIG. 11. The point at which the injection would typically start corresponds, at least roughly, with the interaction of the tongue 140 with the protrusion 162. That is, the protrusion can provide an indication that the injection is starting—for example either that the injection is about to start, that it is starting, or it has just started, depending on the exact relative positions of the various parts of the medicament delivery device.

During the actual injection, the medicament delivery member guard, the rotator and the outer housing would typically be stationary relative to one another. Once the injection is finished (which is typically indicated by an end click generated elsewhere within the medicament delivery device), the medicament delivery device is removed from the injection site, and the medicament delivery member guard will move axially relative to the rotator and the outer housing in the opposite direction to the initial relative movement. As a result, the protrusion will move back along the second pathway and into the third pathway 138. The final position of the protrusion after injection would typically be at or near the position shown in a dashed line and indicated with the reference numeral 163 in FIG. 10.

An example of the interaction between a protrusion 162 and a tongue 140 is shown in FIG. 11. Initially, at position 1, the protrusion 162 abuts the tongue but has not yet started to move the tongue. In position 2, the protrusion has moved in the axial direction and has displaced the tongue in the radial direction. As the protrusion continues to move in the axial direction, it moves past the tongue, as shown in position 3. As the protrusion then begins to move beyond the tongue, position 4, a gap opens up between the tongue and the protrusion, which is then closed as the tongue moves (flexes) back to its original position, hitting the protrusion to cause a click to indicate the start of injection.

The force required by the user to move the protrusion from position 1 to position 2 would be greater than the force required subsequently, due to the force needed to deform the tongue in the radial direction. Once the obstacle provided by the tongue is overcome, the force applied by the user will be greater than the force required to continue to move the protrusion in the axial direction, resulting in significantly faster movement of the protrusion relative to the tongue from position 2 to position 4, which would result in (or help with) creating a gap between the tongue and the protrusion (as the protrusion moves quickly relative to the tongue across the distances D1 and D2 shown in FIG. 11), which allows the tongue to spring back into position and build up speed relative to the protrusion and cause a click by hitting the protrusion (position 5).

In FIG. 11, the protrusion is shown as not deforming and the tongue is shown as deforming. Alternatively, the tongue could remain in place while the protrusion deforms. Alternatively, both the tongue and the protrusion could deform. Depending on the shape of the tongue, the protrusion and other surrounding parts, the tongue could additionally or alternatively hit something other than the protrusion to cause the click, such as another part of the medicament delivery member guard or the rotator. Alternatively or additionally, the click could be caused by the protrusion springing back into position and hitting the tongue, a portion of the rotator 110 such as the surface of the track 132 or a distal portion 131 of the ridge 130 (see FIG. 8). In such cases, the tongue does not necessarily flex at all. The tongue therefore no longer needs to be able to flex relative to the rest of the rotator, and the tongue could alternatively be described as a protrusion of the rotator. There would also be no need to provide an opening in the surface of the track around the tongue.

The rotator 110 extends in an axial direction 120 relative to an axis 122 and in a circumferential direction 124 around the axis. In the Figures, the rotator is shown extending entirely around the axis in the circumferential direction, so 360 degrees around the axis, but the rotator could also extend only part of the way round the axis. Various other structural features of the rotator can be seen in the example in FIG. 8, but these features are not essential to the present disclosure described herein. The rotator could be made as a single integral piece or as several pieces joined together. The rotator is shown as comprising two tracks (two labyrinths) opposite one another relative to the axis 122 (see FIG. 12 for example), but one, three or more tracks could be provided on the rotator.

The ridge 130 can be one single ridge or alternatively two or more separate portions adjacent to one another or spaced apart from one another. Some or all of the ridge or ridges can have further functions, such as providing structural support for the rotator. The ridge in FIG. 8 could be considered to be a single ridge. The ridge in FIG. 8 is shown as a series of straight sections, but the specific shape of the ridge shown in FIG. 8 is not essential; for example, curved portions could be used instead. The track 132 is shown extending from the distal end of the rotator to the proximal end of the rotator, but the track can also be spaced apart from the distal end of the rotator and/or the proximal end of the rotator. In general, the track described in this application can be considered as a volume of space in which the protrusion can move bounded by the ridge. The surface of the track (which is the surface of the rotator adjacent to the track) would typically also limit movement of the protrusion in practice, although this is not necessarily required for the present disclosure to function. When assembled within a complete medicament delivery device, the track would typically also be physically bounded opposite the surface of the track, e.g. by an outer housing, although this is also not necessarily needed to keep the protrusion within the track. The pathway at the distal end of the track is typically aligned in the axial direction with only one of the two pathways at the proximal end of the track.

The opening 139 in the surface of the track allows the tongue 140 to move relative to the rest of the rotator. The surface of the track is the surface of the rotator between the ridges that form the shape of the track. In the case of the example shown in FIG. 8, the track is on the outside surface of the rotator, i.e. the surface of the rotator facing away from the axis 122, with the protrusion 162 extending from the medicament delivery member guard towards the axis in the radial direction. Alternatively, the track could be on the inside surface of the rotator, with the protrusion extending from the medicament delivery member guard away from the axis in the radial direction. The protrusion 141 of the tongue of the rotator 110 is shown extending away from the axis 122 relative to the surface of the track 132, though it could also extend towards the axis in examples where the track is on the inside surface of the rotator.

The tongue 140 is shown in FIG. 11 as deforming in the radial direction. However, in some examples, the tongue could additionally or alternatively be deformed in the circumferential direction and/or the axial direction, depending for example on the shape of the tongue, the location of the tongue in the track and the shape of the protrusion.

The tongue typically extends primarily in the axial direction as shown in FIG. 8, for example, extending from a proximal end to a distal end, though it could also extend in other directions. In the example in FIG. 8, the proximal end of the tongue is attached to the rest of the rotator, with the distal end free to move relative to the rest of the rotator. Various alternatives are available instead of this particular solution. For example, the distal end could be fixed to the rotator and the proximal end free to move, or the tongue could extend in the circumferential direction rather than the distal direction.

The location of the tongue 140 may be varied depending on the shape and relative location of other parts of a medicament delivery device, as different devices may require a somewhat different location to provide a click at the right time during injection (a first click at or near the start of injection). The proximal end 147 and the distal end 148 of the tongue may therefore be in different locations than those shown in the Figures. In the example in FIG. 9, the proximal end 147 of the tongue 140 is adjacent to the transition portion 135 of the first pathway in the axial direction, whereas in the example in FIG. 10, the proximal end of the tongue is spaced apart from the transition portion of the first pathway in the axial direction.

The protrusion 141 (as indicated in FIG. 11 and in FIG. 12, for example) is on the tongue in the examples shown herein. When the protrusion 141 is on the tongue, it could be in various places on the tongue. Typically, the protrusion (or at least part of the protrusion) is spaced apart from the place where the tongue is attached to the rotator; this allows the tongue to flex relative to the rotator when the protrusion of the medicament delivery member guard acts on the protrusion. For example, the protrusion may extend from the end of the tongue distal from the place where the tongue is attached to the rotator. However, as mentioned above, the protrusion does not necessarily need to move at all relative to the rest of the rotator, and as such it is not essential that the tongue flexes. The tongue itself is also not essential. In such cases, the protrusion 141 extends from the surface of the track, and there is no need for a tongue 140 or an opening 139. The tongue and the protrusion on the tongue could be shaped in various other ways, for example by angling the tongue so that the cross-section in the view of FIG. 12 (parallel to the axis) is a V shape (with the protrusion being at the centre of the V) rather than the relatively triangular shape shown in the example in FIG. 12. The same concepts as described above for the protrusion 141 could additionally or alternatively be used to replace the second tongue with a protrusion. In general, the sloped portions described herein are sloped relative to the surface of the track 132. The sloped portions may be planar. Alternatively, the sloped portions may be another shape; for example, they may be curved in one or more directions. The sloped portions can be described as angled relative to the surface of the track 132. One way of quantifying this is shown in FIGS. 5 and 6. The angle A1, A2 shows the angle described by the surface of the track and the sloped portion. Where a slope is provided, the angle is more than 90 degrees and less than 180 degrees, for example between 105 and 165 degrees or between 120 and 165 degrees, for example 150 degrees. The angle A1 in FIG. 12 is the angle between the first sloped portion 142 of the tongue 140 and the surface of the track 132. The first sloped portion 142 is angled relative to the surface of the track and is angled towards the proximal end 114 of the rotator 110. Similarly, the angle A2 in FIG. 13 is the angle between the second sloped portion 144 of the tongue 140 and the surface of the track 132. The second sloped portion 144 is angled relative to the surface of the track and is angled towards the distal end 116 of the rotator 110. In this example, the first sloped portion and the second sloped portion are both sloped at the same angle, but they can alternatively be sloped at different angles. The distal end of the first sloped portion typically extends further from the axis than the proximal end of the first sloped portion. Similarly, the proximal end of the second sloped portion typically extends further from the axis than the distal end of the second sloped portion.

The third sloped portion 146 is angled towards the proximal end 114 of the tubular body 112 and is also angled towards the part of the pathway labelled as pathway 134 in FIG. 10—in other words, it is angled in the axial direction and also the circumferential direction. This slope is not provided in all embodiments, but can be provided to allow the protrusion to climb onto the tongue more smoothly, particularly in examples where part or all of the tongue overlaps with the first pathway (or specifically with the transition portion of the first pathway) in the axial direction.

A second tongue 150 can be provided in a second opening 149 in the track, as shown for example in FIGS. 8 and 9. The second tongue would typically be partially or entirely in the third pathway. In contrast to the tongue 140, which has first and second sloped portions to allow the protrusion to pass over the tongue in both directions (i.e. in either direction in the axial direction), the second tongue 150 is designed to only allow the protrusion 162 to move in one direction, and not in the other. Once the protrusion has gone past the second tongue 150 (so that the protrusion is in the third pathway 138 in a position closer to the proximal end 114 of the rotator than the position of the second tongue), the protrusion is unable to pass back in the distal direction as the second tongue blocks it. This can provide a medicament delivery member guard lock, which can shield the medicament delivery member after use and avoid issues such as needle stick injuries.

The second opening 149 in the surface in the track can be spaced apart from the opening 139 as shown in FIG. 8, or the opening 139 and the second opening 149 can be combined into a single opening. Similarly, the tongue 140 and the second tongue 150 can be spaced apart from one another as shown in FIG. 8, or can be combined into a single structure.

The medicament delivery member guard comprises a protrusion 162, which may take various shapes other than the shape shown in the examples in the Figures.

Another part of the disclosure relates to a feedback mechanism for a medicament delivery device and more particularly to the feedback mechanism for indicating a delivery operation of the medicament delivery device.

Medicament delivery devices such as auto-injectors, inhalers, on-body devices are generally known for the self-administration of a medicament by patients without formal medical training. For example, those patients suffering from diabetes or those people taking the artificial fertilization procedure may require repeated injections of insulin or hormone. Other patients may require regular injections of other types of medicaments, such as a growth hormone.

Since those medicament delivery devices are designed for patients without formal medical training, operations of those medicament delivery devices might be taken place in patients' house, which is usually not in a place of professional health/medical care, e.g. hospital, clinic or heath centres. There is a demand of providing users of medicament delivery devices a feedback in response to different stages of every single delivery operation that is taken by users. The feedback can help the user to handle the medicament delivery device, or it can be detected and every single delivery operation that is taken by the user can be recorded to help the user to track his/her medicament intake or as the basis of an alarm as the next operation reminder and/or help a medical doctor or a health care provider to track the compliance of the user regarding to the therapeutic regimen.

The document WO 2011/123024 discloses a medicament delivery device provided with a number of automatic functions, which medicament delivery device has been very well received on the market. The medicament delivery device comprises a feedback mechanism with a signal generating member adapted to generate an audible and/or tactile and/or visible injection confirmation signal upon a performed medicament delivery.

In most instances this solution works very well. However, there is also a demand to indicate the user of the medicament delivery device about the initiation of the medicament delivery operation.

The present concept is directed to a feedback mechanism for a medicament delivery device and will now be described more fully hereinafter with reference to the accompanying drawings, in which exemplifying embodiments are shown. The feedback mechanism may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 14:
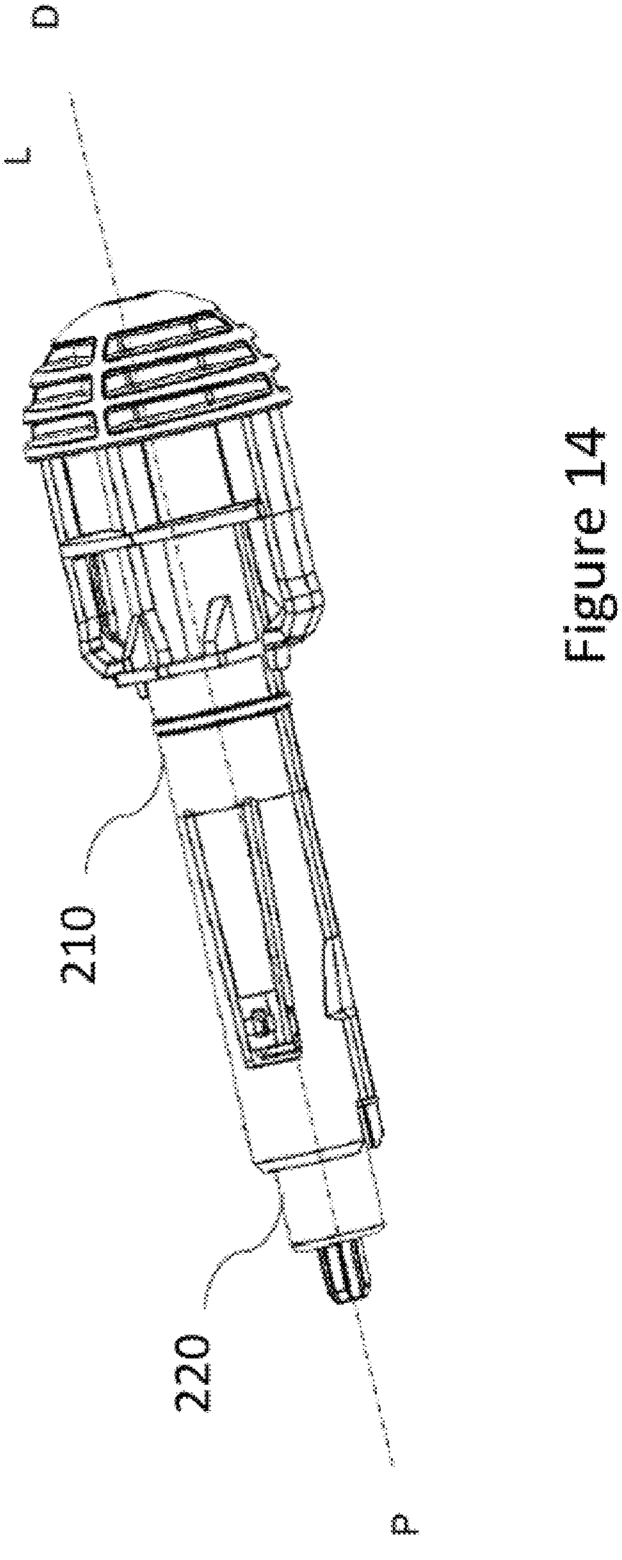
FIG. 14 displays a power pack of a medicament delivery device comprising a feedback mechanism.
Figures 15A, 15B:
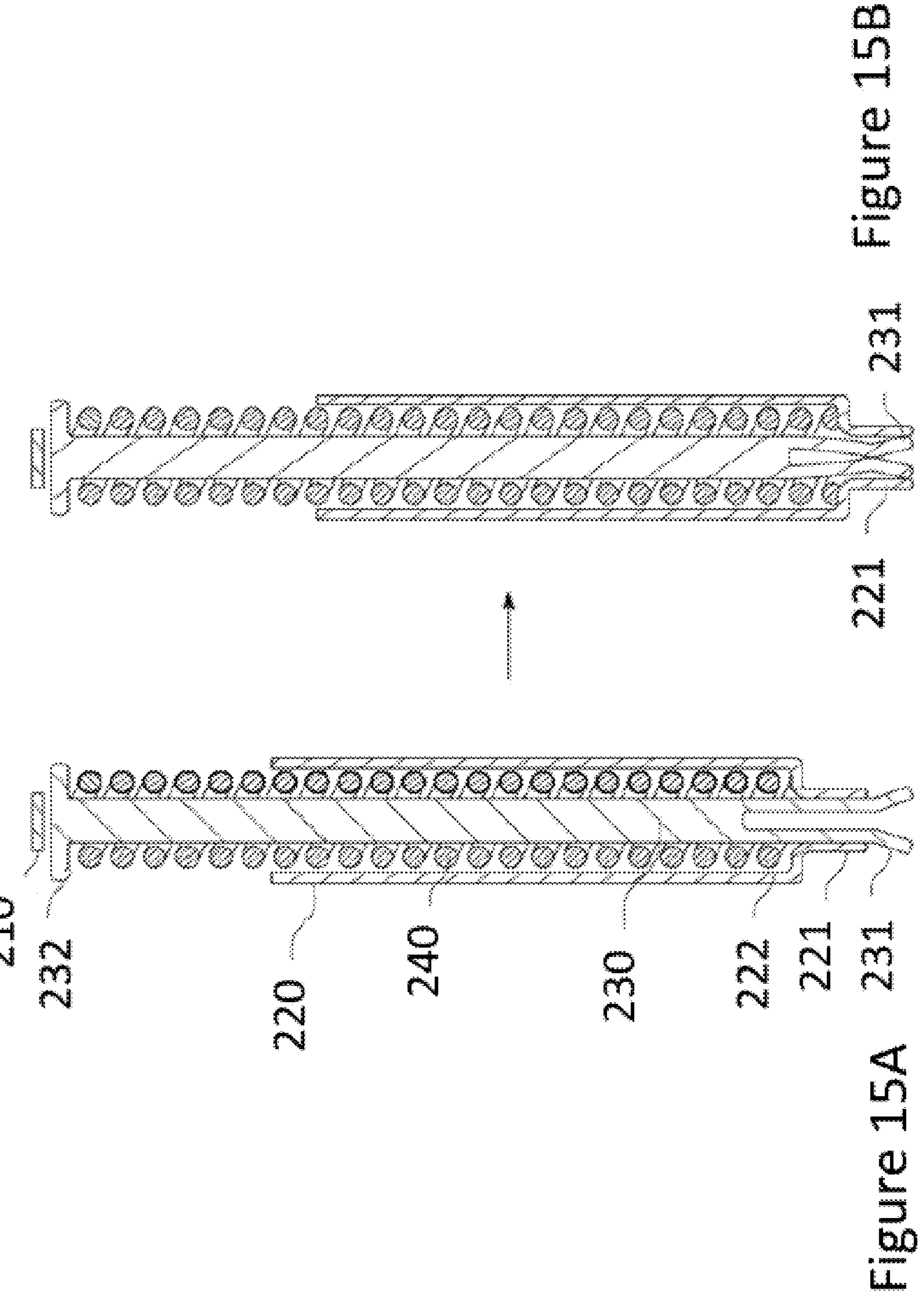
FIG. 15A-15B display the cross-section view of a first embodiment of a feedback mechanism that can be implemented in the power pack of FIG. 1.

FIG. 14 illustrates a feedback mechanism in a first embodiment which comprises a housing 210 having a proximal end P, a distal end D, and extending along a longitudinal axis L and a plunger rod 220 received in the housing 210 in an initial position of the plunger rod 220 which the axial movement of the plunger rod 220 is prevented. As shown in FIG. 15A, the feedback mechanism further comprises a feedback element 230 arranged within an inner space of the plunger rod 220; and a drive member 240, preferably a resilient member as a spring. One end of the drive member is supported by an inner support surface 232 of the feedback element 230 at its distal end and the other end of the drive member is supported by an inner shoulder 222 of the plunger rod 220 at its proximal end. The drive member 240 is configured to proximally bias the plunger rod 220 in relation to the housing 210 and the feedback element 230.

It should be noted that, alternatively, the feedback element may be arranged between the plunger rod 220 and the housing 210, as shown in FIG. 15A; or, in another embodiment, the feedback element may be arranged between the plunger rod 220 and may be a second feedback element configured to generate a second feedback once the plunger rod 220 reaches a predetermined proximal position.

The feedback element 230 is integral to the housing 210 or fixed to the housing 210 by a backlash force of the drive member 240. The feedback element 230 comprises a resilient portion 231, preferably, a pair of resilient arms 231 and may further comprise a guide member, preferably a rod member; configured to radially support drive member 240.

The plunger rod 220 comprises an interaction member 221, preferably, a tubular recess 221. The pair of resilient arms 231 is configured to extend through the tubular recess 221 and extend radially outward in relation to the plunger rod 220 in the initial position of the plunger rod 220.

Once a delivery operation is initiated, the plunger rod 220 is forced to move proximally under the biasing force from the drive member 240. The proximal movement of the plunger rod 220 causes the tubular recess 221 pass through the pair of resilient arms 231. Once the tubular recess 221 pass through the pair of resilient arms 231, it forces the pair of resilient arms 231 to move radial inwardly and the pair of resilient arms 231 will then make contact as shown in FIG. 15B. The contact of the pair of resilient arms 231 generates an audible feedback to a user of the medicament delivery device.

The contact of the pair of resilient arms 231 may also establish an electronic connection between the pair of resilient arms 231. Such as the feedback element 230 may be arranged with a circuit with two electrodes that the electronic connection in between will be established by the contact of the pair of resilient arms 231. The circuit may further arrange a visual indicator, such as a LED; an audible indicator, such as a buzzer and/or a haptic indicator, such as a vibration unit; so that the user of the medicament delivery device can get an indication of the initiation of the delivery operation. The circuit may further comprise a communication unit, such as RFID, Bluetooth, Zigbee, GPRA, 3G, 4G or 5G, so that a signal in response to the initiation of the delivery operation may be sent to a local computing device, such as a smart phone or a remote computing device, such as a cloud server.

Figures 16A, 16B, 16C:
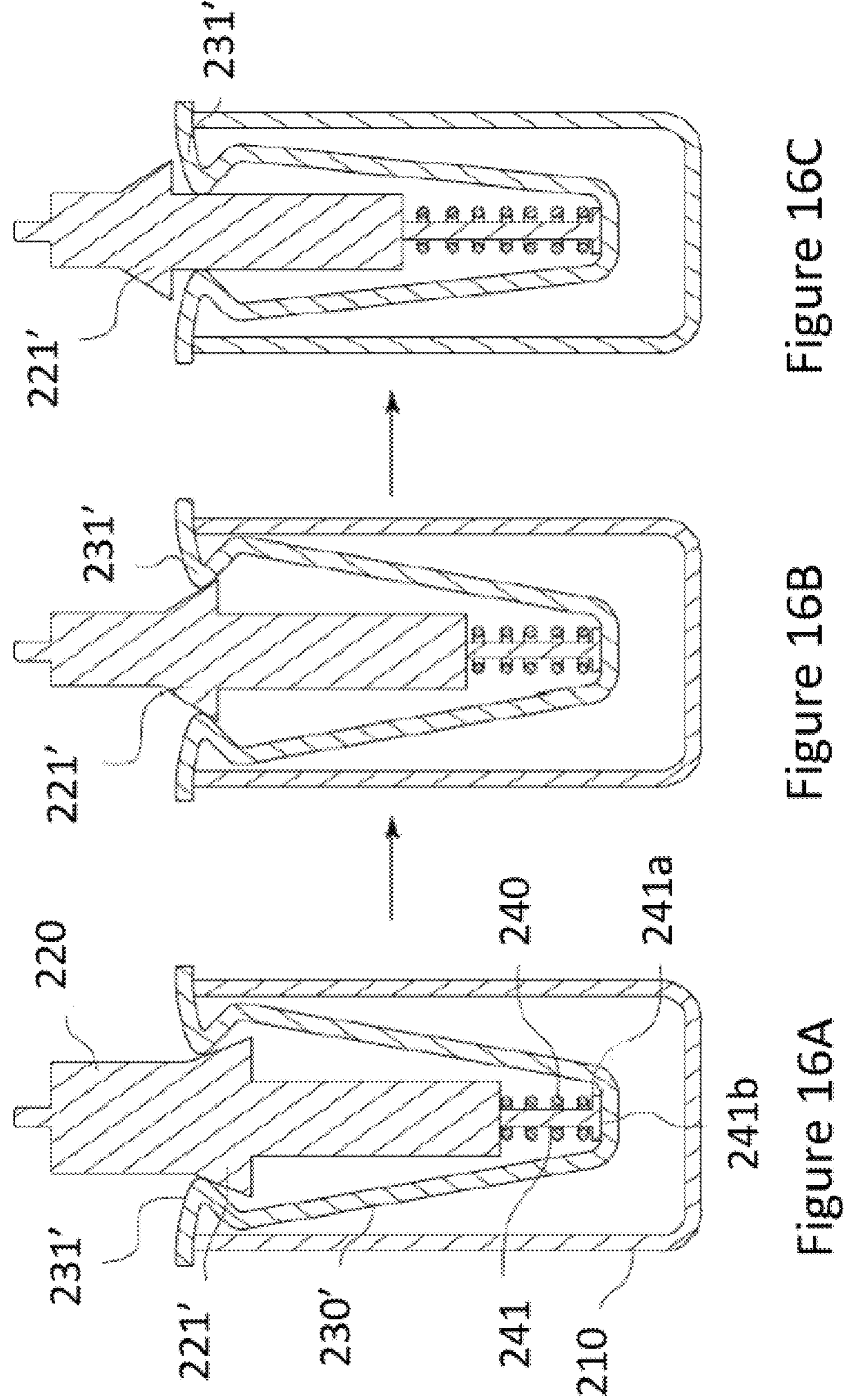
FIG. 16A-16C display a cross-section view of a second embodiment of feedback mechanism that can be implemented in the power pack of FIG. 1.

FIG. 16A-16C illustrate the second embodiment of the feedback mechanism. The arrangement between the housing 210, plunger rod 220 and the drive member 240 is the same as described in the first embodiment. The drive member 240 is arranged between the plunger rod 220 and the distal end of the feedback element 230', such that the drive member 240 is configured to proximally bias the plunger rod 220 and distally bias the feedback element 230'. A guide member, preferably a rod member 241 is arranged to radially support drive member 240 and comprise an inner support surface 241*a* which is configured to engage with the distal end of the drive member 240 and an outer support surface 241*b* configured to engage with an inner distal end of the feedback element 230'. The feedback element 230' in the second embodiment can be fixed or integral to the housing 210; or releasably fixed to the housing 210 when the plunger rod 220 is in the initial position and during the delivery operation of the medicament delivery device. The feedback element 230' comprises at least one longitudinally extending resilient arm comprising a contact portion 231' that is configured to radially bias on the plunger rod 220. The feedback element 230' can be fixed or integral to the housing 210; or releasably fixed to the housing 210 when the plunger rod 220 is in the initial position and during the delivery operation of the medicament delivery device.

The interaction member of the plunger rod 220 in the second embodiment comprises a radial outwardly extending protrusion 221' arranged on its outer surface. The protrusion 221' is distally arranged in relation to the contact portion 231' when the plunger rod 220 is in its initial position as shown in FIG. 16A. Once a delivery operation is initiated, the plunger rod 220 is moved proximally under the biasing force from the drive member 240. The proximal movement of the plunger rod 220 causes the radial outwardly extending protrusion 221' pass through the contact portion 231' on the feedback element 230'. Once the radial outwardly extending protrusion 221' passes through the contact portion 231', the contact portion 231' is flexed radially outward as shown in FIG. 16B. After the radial outwardly extending protrusion 221' passes through the contact portion 231' with the proximal movement of the plunger rod 220, the contact portion 231' flexes back and snaps on the outer surface of the plunger rod 220 as shown in FIG. 16C, thereby an audible feedback is generated.

Figures 17, 18:
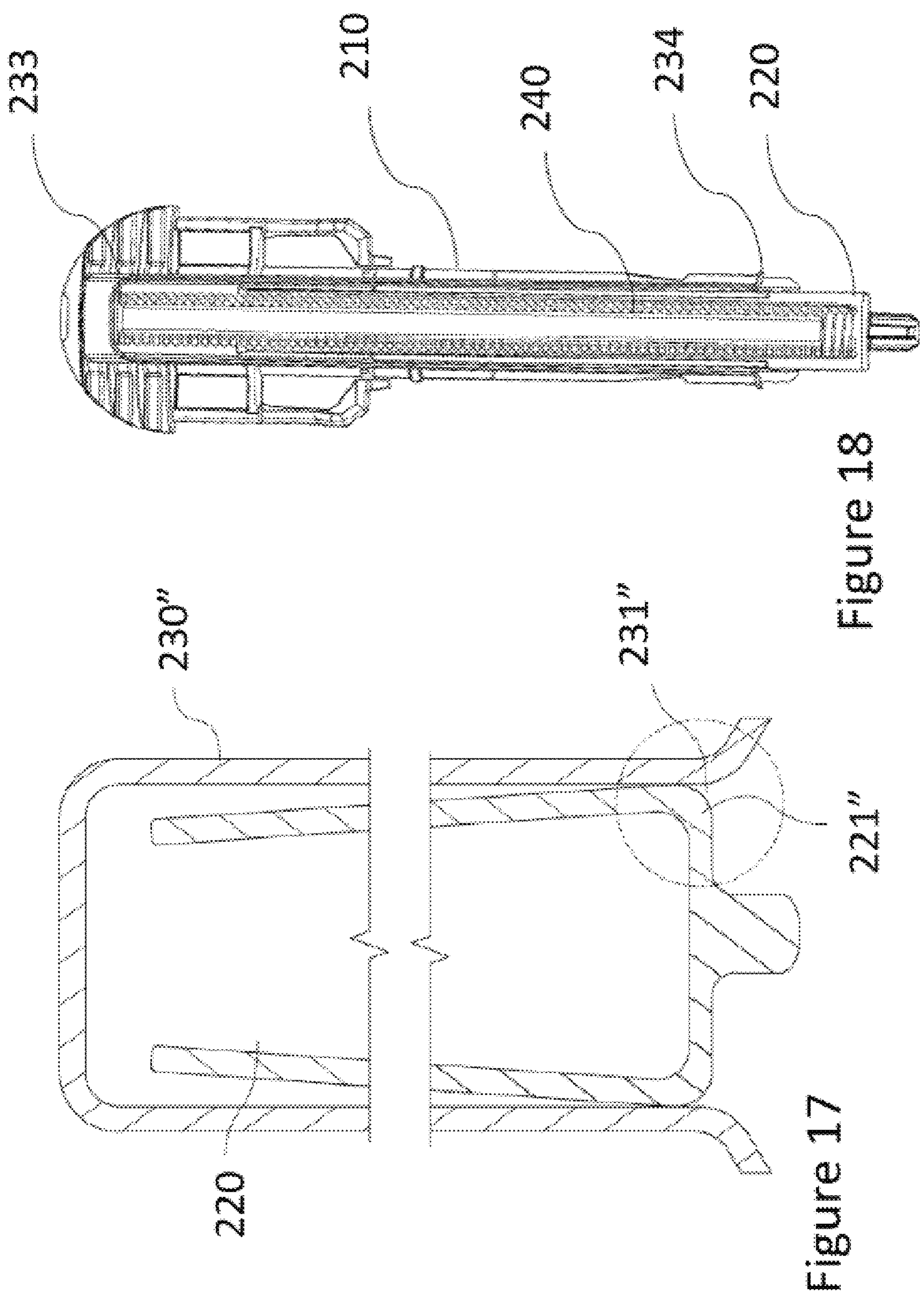
FIG. 17 displays a cross-section view of a third embodiment of a feedback mechanism that can be implemented in the power pack of FIG. 1.
FIG. 18 displays a cross-section view of the power pack of FIG. 1 having a retaining member that can be implemented in the second and the third embodiments.

FIG. 17 illustrates the third embodiment of the feedback mechanism. The arrangement between the housing 210, plunger rod 220 and the drive member 240 is same as described in the first embodiment. The drive member 240 is also arranged between the plunger rod 220 and the distal end of the feedback element 230" as described in the second embodiment. The feedback element 230" in the third embodiment comprises a longitudinal extending resilient arm with a counter contact portion 231". The counter contact portion 231" configured to contact with the outer surface of the plunger rod 220; more preferably, to contact with a contact portion 221" arranged on the outer surface of the plunger rod 220. The contact portion 221" on the plunger rod 220 and the counter contact portion 231" of the feedback element 230" is made by the same plastic material or one of the contact portion 221" or the counter contact portion 231" is made by or coated with a large molecular and high viscous material, such as resin. The friction between the contact portion 221" and the counter contact portion 231" is thereby increased.

Once a delivery operation is initiated, the plunger rod 220 is moved proximally under the biasing force from the drive member 240. The proximal movement of the plunger rod

220 causes the contact portion 221" to move relative to the counter contact portion 231". The high friction generated by the relative movement between the contact portion 221" and the counter contact portion 231" causes the longitudinal extending resilient arm to vibrate within the housing 210, such that an audible feedback is generated to the user of the medicament delivery device to indicate the initiation of the medicament delivery device.

The feedback element 230'; 230" in the second and the third embodiments may further be arranged with a retaining member 234 which is configured to releasably connect to a counter retaining member of the housing 210 as shown in FIG. 18.

Figures 19A, 19B, 19C:
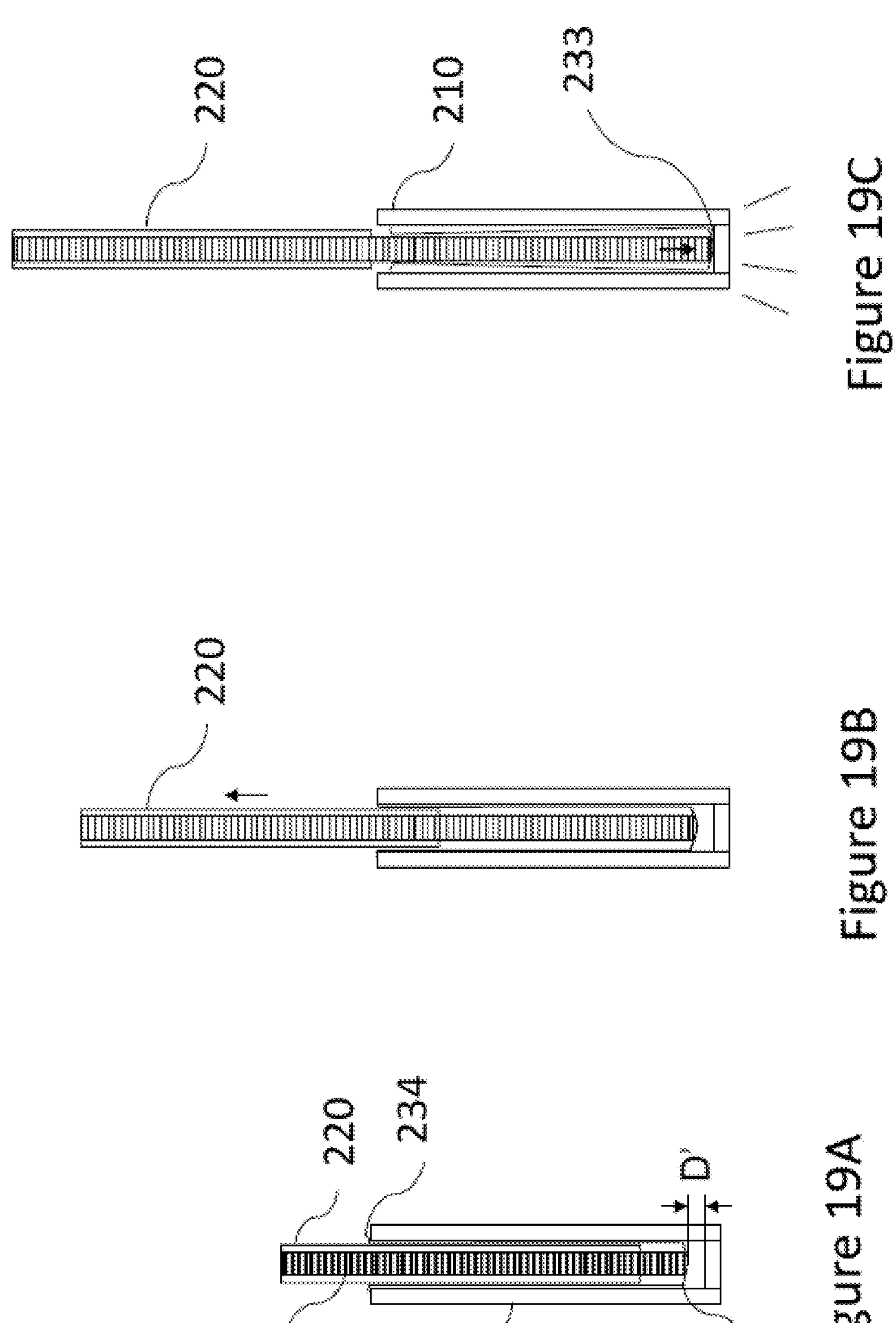
FIG. 19A-19C display a sequence of generating a second feedback that can be implemented in the power pack of FIG. 1.

The feedback element 230'; 230" is arranged between the inner surface of the housing 210 and the outer surface of the plunger rod 220. A gap D' is defined by the distal end 233 of the feedback element 230'; 230" and the housing 210 at the initial position of the feedback element 230'; 230" as shown in FIG. 19A-19B.

The retaining member 234 is configured to extend radially outward in relation to the counter retaining member of the housing 210, such that the distal axially movement of the feedback element 230'; 230" is prevented. An interface formed between the retaining member 234 of the feedback element 230'; 230" and the counter retaining member of the housing 210 is formed with a predetermined angle in relation to the longitudinal axis L. Such angular interface causes a retaining force exerted by the counter retaining member of the housing 210 be divided into a proximally axial dividing force and a radial inward dividing force. Therefore, once the plunger rod 220 is released and moved proximally and the outer surface of the biased plunger rod 220 is no longer in contact with the feedback element 230'; 230", the retaining member 234 of the feedback element 230'; 230" will be biased inward due to the radial inward dividing force, such that the retaining member 234 is disengaged from the counter retaining member of the housing 210.

Once the retaining member 234 is disengaged from the counter retaining member of the housing 210, the feedback element 230'; 230" is distally biased by the drive member 240 and the distal end 233 of the feedback element thereby hits on the inner surface of the housing 210, such that a second feedback is generated.

In an alternative embodiment, the second feedback can be arranged that the hitting action of the feedback element to switch on a switch of an electronic circuit arranged on the distal end of the housing 210 provides the second feedback as a visual, audible or haptic format indication to the user of the medicament delivery device to indicate an end of the delivery operation of the medicament delivery device.

In an alternative embodiment, instead of the second feedback, the feedback mechanism as described in the second and the third embodiment may be arranged to indicate the process of the delivery operation. The second embodiment can be arranged with a plurality of protrusion 221' on the outer surface of the plunger rod 220 or the contact portion 231' on the feedback element 230'. In the third embodiment, the length of the contact between the contact portion 221" and the counter contact portion 231" can be arranged of equal length as of the plunger rod 220.

Various modifications to the embodiments described are possible and will occur to those skilled in the art without departing from the present disclosure which is defined by the following claims.

The invention claimed is:

1. A rotator for a medicament delivery device, the rotator comprising:

a tubular body extending from a proximal end to a distal end in an axial direction relative to an axis;

one or more ridges extending from a surface of the tubular body, the one or more ridges defining a track on the surface of the tubular body, the track extending in the axial direction from a distal end of the track to a proximal end of the track, the track comprising one pathway at the distal end of the track and two pathways at the proximal end of the track, wherein the two pathways at the proximal end of the track are separated by at least one of the one or more ridges; and a protrusion extending from a surface of the track, the protrusion comprising a surface extending in the track, the surface of the protrusion comprising a first sloped portion and a second sloped portion closer to the distal end of the tubular body than the first sloped portion, wherein the first sloped portion and the second sloped portion are angled relative to the surface of the track, wherein the first sloped portion is angled towards the proximal end of the tubular body and the second sloped portion is angled towards the distal end of the tubular body, wherein the rotator comprises a first tongue configured to allow a protrusion of a medicament delivery member guard to move over the first tongue in two directions, and a second tongue configured to allow the protrusion of the medicament delivery member guard to move over the second tongue in one direction, wherein the protrusion is on the first tongue, wherein the first tongue extends in an opening in the surface in the track, and wherein the first tongue is configured to flex relative to the surface of the track.

2. The rotator of claim 1, wherein the first tongue extends in the axial direction from a proximal end to a distal end, and the proximal end of the first tongue is attached to the tubular body and the distal end of the first tongue is configured to flex relative to the surface of the track.

3. The rotator of claim 1, wherein the first tongue extends in the axial direction from a proximal end to a distal end, and the distal end of the first tongue is attached to the tubular body and the proximal end of the first tongue is configured to flex relative to the surface of the track.

4. The rotator of claim 1, wherein the surface of the tubular body faces away from the axis of the rotator, and wherein the one or more ridges extend from the surface.

5. The rotator of claim 1, wherein the distal end of the first sloped portion extends further from the axis than the proximal end of the first sloped portion.

6. The rotator of claim 1, wherein at least part of the first sloped portion extends further from the axis than the surface of the track.

7. The rotator of claim 1, wherein the second tongue extends in an opening in the surface in the track.

8. The rotator of claim 7, wherein the second tongue extends in the axial direction from a proximal end to distal end, and wherein the distal end of the second tongue is attached to the tubular body and the proximal end of the second tongue is configured to flex relative to the surface of the track.

9. The rotator of claim 1, wherein the angle between the first sloped portion and the surface of the track is between 105 and 165 degrees, and wherein the angle between the second sloped portion and the surface of the track is between 105 and 165 degrees.

10. The rotator of claim 1, wherein the surface of the protrusion comprises a third sloped portion adjacent to the first sloped portion, wherein the third sloped portion is sloped towards the proximal end and is sloped in a circumferential direction relative to the axis.

11. The rotator of claim 1, wherein the pathway at the distal end of the track is aligned in the axial direction with only one of the two pathways at the proximal end of the track.

12. The rotator of claim 1, wherein the protrusion is closer to the distal end of the rotator than to the proximal end of the rotator.

13. A medicament delivery device comprising the rotator of claim 1.

14. The medicament delivery device of claim 13, comprising a housing extending from a proximal end to a distal end in the axial direction and extending in a circumferential direction around the axis and the medicament delivery member guard, wherein the rotator is in the housing, and wherein the rotator is able to move in the circumferential direction within the housing during use of the medicament delivery device, wherein the medicament delivery member guard is in the housing, and wherein the medicament delivery member guard is able to move in the axial direction within the housing during use of the medicament delivery device, wherein the protrusion of the medicament delivery member guard is arranged in the track of the rotator.

15. A rotator for a medicament delivery device, the rotator comprising:

a tubular body having a proximal end and a distal end and an axis;

a plurality of ridges extending from a surface of the tubular body that define a track on the surface of the tubular body, where the track comprises a first, second and third pathway, where a transition pathway separates the first and second pathway;

a first flexible tongue configured to allow a protrusion of a medicament delivery member guard to move over the first flexible tongue in two directions, where the first flexible tongue is located in the second pathway, and where the first flexible tongue comprises a first protrusion extending outward relative to the surface of the track; and a second flexible tongue configured to allow the protrusion of the medicament delivery member guard to move over the second flexible tongue in one direction, where the second flexible tongue is located in the third pathway, and where the second flexible tongue comprises a second protrusion extending outward relative to the surface of the track, wherein the first and third pathways are located at the proximal end of the rotator, wherein the first and second flexible tongues extend into openings formed from cut outs in the surface of the track, and wherein the first protrusion interacts with the medicament delivery member guard at a start of medicament delivery and the second protrusion interacts with the medicament delivery member guard after the delivery of medicament is completed.

16. The rotator of claim 15, wherein the second flexible tongue extends in an axial direction from a proximal end to distal end, and wherein the distal end of the second flexible tongue is attached to the tubular body and the proximal end of the second flexible tongue is configured to flex radially inward relative to the surface of the track.

17. The rotator of claim 15, wherein the surface of the first protrusion comprises a first sloped portion and a second sloped portion closer to the distal end of the tubular body than the first sloped portion, wherein the first sloped portion and the second sloped portion are angled relative to the surface of the track.

* * * * *